US012643898B2

(12) United States Patent
Li et al.

(10) Patent No.: US 12,643,898 B2
(45) Date of Patent: Jun. 2, 2026

(54) METHOD FOR SYNTHESIZING ANTI-TUMOR COMPOUND AND INTERMEDIATES THEREOF

(71) Applicant: Transthera Sciences (Nanjing), Inc., Nanjing (CN)

(72) Inventors: Lin Li, Nanjing (CN); Sishun Kang, Nanjing (CN); Zhonghui Wan, Nanjing (CN)

(73) Assignee: TransThera Sciences (Nanjing), Inc., Nanjing (CN)

( * ) Notice: Subject to any disclaimer, the term of this patent is extended or adjusted under 35 U.S.C. 154(b) by 731 days.

(21) Appl. No.: 17/998,231

(22) PCT Filed: May 8, 2021

(86) PCT No.: PCT/CN2021/092315
§ 371 (c)(1),
(2) Date: Nov. 8, 2022

(87) PCT Pub. No.: WO2021/223751
PCT Pub. Date: Nov. 11, 2021

(65) Prior Publication Data

US 2023/0212167 A1 Jul. 6, 2023

(30) Foreign Application Priority Data

May 8, 2020 (CN) ......................... 202010390390.3

(51) Int. Cl.
*C07D 471/14* (2006.01)

(52) U.S. Cl.
CPC .................................. *C07D 471/14* (2013.01)

(58) Field of Classification Search
CPC .................................................... C07D 471/14
See application file for complete search history.

(56) References Cited

U.S. PATENT DOCUMENTS

| | | | |
|---|---|---|---|
| 6,440,959 | B1 | 8/2002 | Ding et al. |
| 6,838,558 | B2 | 1/2005 | Ding et al. |
| 6,916,923 | B2 | 7/2005 | Ding et al. |
| 2002/0183514 | A1 | 12/2002 | Ding et al. |
| 2004/0198976 | A1 | 10/2004 | Ding et al. |
| 2019/0040064 | A1 | 2/2019 | Wu |

FOREIGN PATENT DOCUMENTS

| | | | | |
|---|---|---|---|---|
| CN | 1348455 A | 5/2002 | | |
| JP | 2019518784 | 7/2019 | | |
| RU | 2249593 | 4/2005 | | |
| WO | 2006040036 | 4/2006 | | |
| WO | WO-2018108079 A1 * | 6/2018 | | C07D 471/14 |
| WO | WO-2021223751 A1 | 11/2021 | | |

OTHER PUBLICATIONS

"EP142728 Extended European Search Report mailed Mar. 5, 2024", 6 pages.
"CA 3182501 Requisition by the Examiner in Accordance With Subsection 86(2) mailed Nov. 26, 2024", 6 pages.
"RU 2022131864 Official Action with Search Report dated Aug. 19, 2024", English translation only, 11 pages.
"TW 110116666 1st OA with Search Report mailed Oct. 11, 2024", with manual English translation, 13 pages.
"JP2023525732A Notice of Reasons for Refusal mailed 1-28-205", with English translation, 10 pages.
"RN 1557979 98-2 and nine other compounds", File 'Registry' Entered at 16:04:30 on Jan. 20, 2025, 9 pages.
Smit, W. A., "Organic Synthesis The Science Behind the Art", Society of Chemistry, 1998, 1 page.
"International Application No. PCT/CN2021/092315, International Search Report mailed Jul. 22, 2021", (Jul. 22, 2021), 7 pgs.
"International Application No. PCT/CN2021/092315, Written Opinion mailed Jul. 22, 2021", (Jul. 22, 2021), 9 pgs.

* cited by examiner

*Primary Examiner* — John S Kenyon
*Assistant Examiner* — Rehana Ismail
(74) *Attorney, Agent, or Firm* — Schwegman Lundberg & Woessner, P.A.

(57) ABSTRACT

The present invention belongs to the technical field of medicines, and particularly relates to a method for synthesizing an anti-tumor compound and intermediates thereof. The synthesis method of the present invention has improved operability and allows for a simplified process, in which higher purity can be achieved without the complicated process of recrystallizing the synthesized target compound, and thus less of the three wastes is produced, making the method more suitable for industrial mass production. Where the intermediates according to the present invention are used for preparing an anti-tumor compound, by-products are effectively reduced during reactions, and thus the overall yield of the reactions are improved, and is at least twice as high as that obtained using the existing synthesis method.

20 Claims, No Drawings

METHOD FOR SYNTHESIZING ANTI-TUMOR COMPOUND AND INTERMEDIATES THEREOF

PRIORITY CLAIM TO RELATED APPLICATIONS

This application is a U.S. national stage filing under 35 U.S.C. § 371 from International Application No. PCT/CN2021/092315, filed on 8 May 2021, and published as WO2021/223751 on 11 Nov. 2021, which claims the benefit under 35 U.S.C. 119 to Chinese Application No. 202010390390.3, filed on 8 May 2020, the benefit of priority of each of which is claimed herein, and which applications and publication are hereby incorporated herein by reference in their entirety.

TECHNICAL FIELD

The present invention belongs to the technical field of medicines, and particularly relates to a method for synthesizing an anti-tumor compound and intermediates thereof.

BACKGROUND

In addition to being associated with the overexpression of mitotic kinases (e.g., Aurora kinases), tumor growth and migration also depend on the formation of large numbers of new blood vessels, in which the VEGF/VEGFR (vascular endothelial growth factor/vascular endothelial growth factor receptor) pathway plays a key role in tumor neovascularization.

Patent WO2018108079A1 discloses a range of compounds capable of inhibiting, modulating and/or regulating the activity of one or more protein kinases such as Aurora kinases and VEGFR kinases, and reversing tumor microenvironments and producing a tumor immune effect and an anti-tumor therapeutic effect by inhibiting tumor growth and migration. The patent describes a method for synthesizing a compound 29. Further research shows that the synthesis process still needs to be optimized so as to obtain a synthesis method that features a simpler process, a higher yield, higher purity and lower costs and is suitable for industrial mass production.

Compound 29

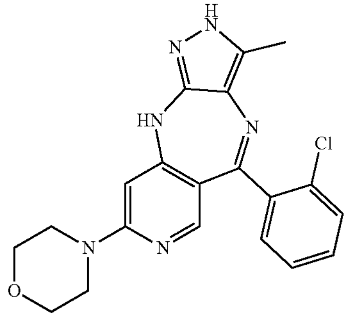

SUMMARY

In a first aspect, the present invention provides the following technical solutions 1-15:

1. a method for synthesizing an anti-tumor compound of formula 7, comprising the following steps:

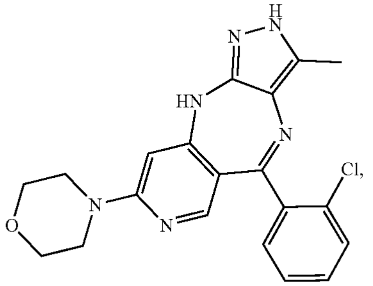

7

(a) subjecting a compound of formula 1 to an aromatic nucleophilic substitution reaction with a compound of formula 2M in an organic solvent under the action of a base to give a compound of formula IM, and subjecting the compound of formula IM separated or not separated to another aromatic nucleophilic substitution reaction with a compound of formula 3, e.g., under alkaline conditions, to give a compound of formula 4M;

(b) subjecting the compound of formula 4M to a reduction reaction in an organic solvent under the action of a catalyst to give a compound of formula 5M;

(c) subjecting the compound of formula 5M to a ring-closing reaction in an organic solvent under the action of an acid to give a compound of formula 6M; and (d) subjecting the compound of formula 6M to a reaction in an organic solvent to remove an amino-protecting group to give the anti-tumor compound of formula 7;

the reaction scheme being as follows:

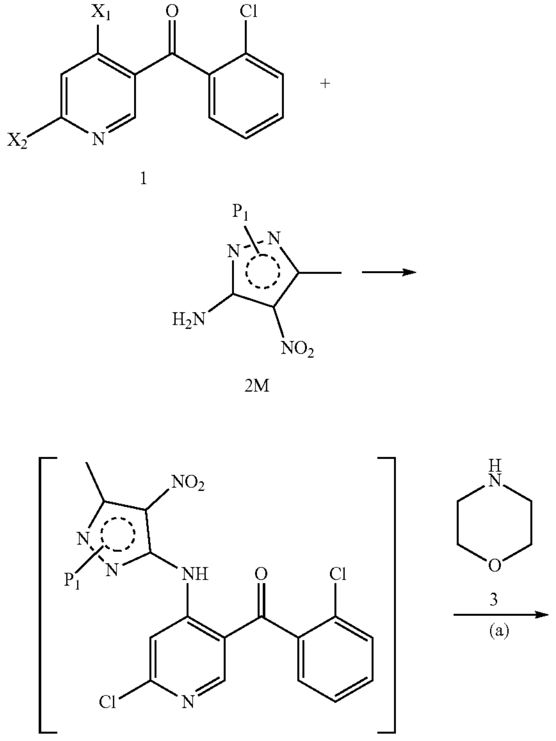

1

2M

IM

3

-continued

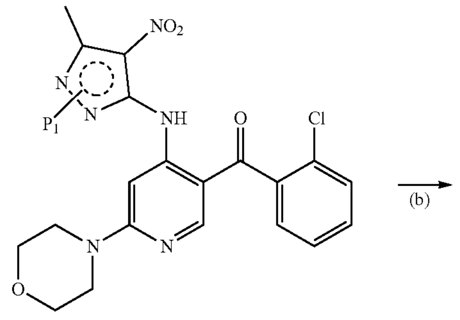

4M

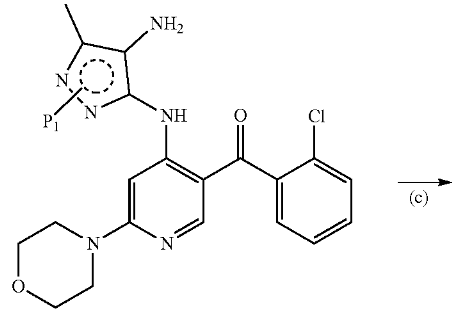

5M

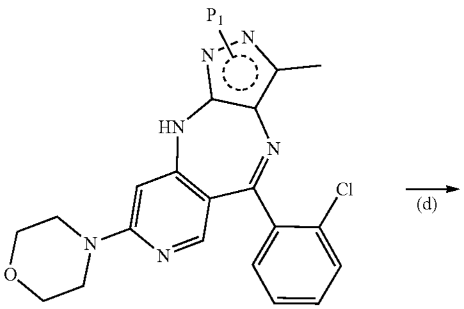

6M

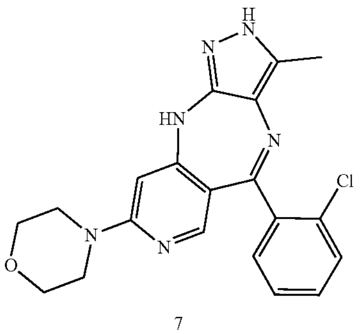

7 wherein $X_1$ and $X_2$ are each selected from halogen; $P_1$ is an amino-protecting group, and preferably, $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located;

2. a method for synthesizing an anti-tumor compound of formula 7,

7

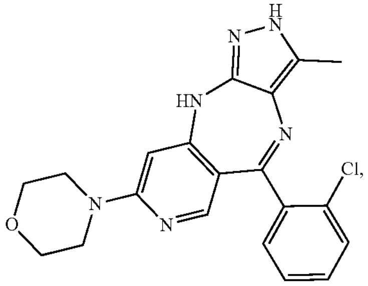

comprising the following step:

(d) subjecting the compound of formula 6M to a reaction in an organic solvent to remove an amino-protecting group to give the anti-tumor compound of formula 7;

the reaction scheme being as follows:

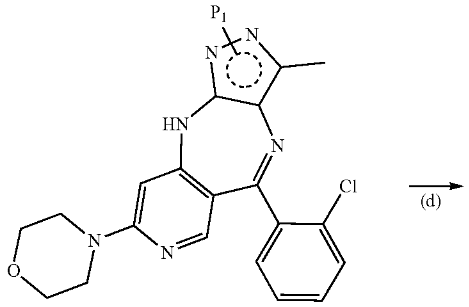

6M

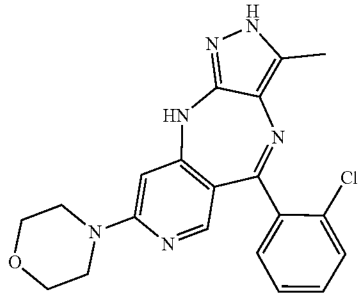

7 wherein $P_1$ is an amino-protecting group, and preferably, $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located;

3. a method for synthesizing an intermediate compound of formula 6M or the method according to any one of the preceding technical solutions,

6M

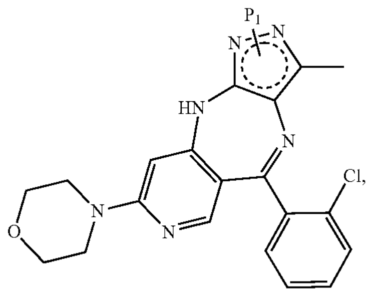

comprising the following step:

(c) subjecting the compound of formula 5M to a ring-closing reaction in an organic solvent under the action of an acid to give a compound of formula 6M;

the reaction scheme being as follows:

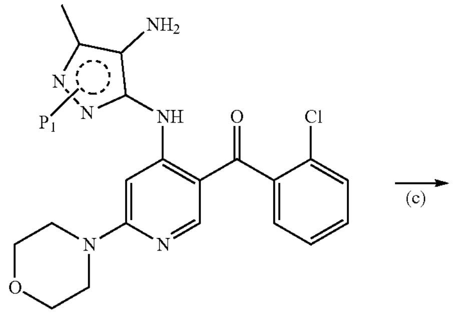

5M

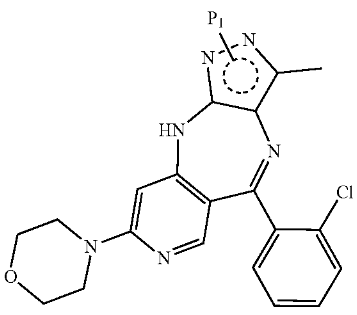

6M wherein $P_1$ is an amino-protecting group, and preferably, $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located;

4. a method for synthesizing an intermediate compound of formula 5M or the method according to any one of the preceding technical solutions,

5M

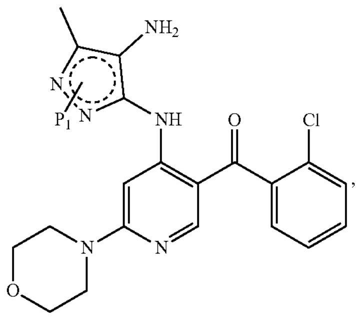

comprising the following step:

(b) subjecting the compound of formula 4M to a reduction reaction in an organic solvent under the action of a catalyst to give a compound of formula 5M;

the reaction scheme being as follows:

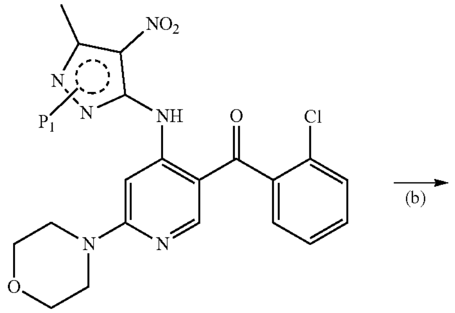

4M

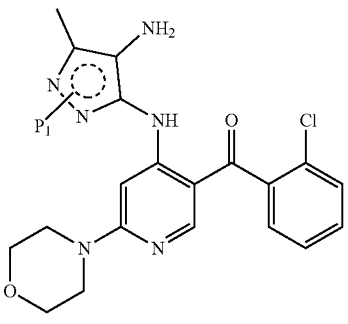

5M wherein $P_1$ is an amino-protecting group, and preferably, $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located;

5. a method for synthesizing an intermediate compound of formula 4M or the method according to any one of the preceding technical solutions,

4M

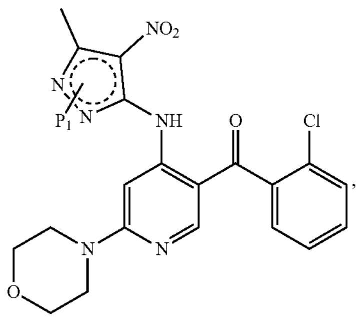

comprising the following step:

(a) subjecting a compound of formula 1 to an aromatic nucleophilic substitution reaction with a compound of formula 2M in an organic solvent under the action of a base to give a compound of formula IM, and subjecting the compound of formula IM separated or not separated to another aromatic nucleophilic substitution reaction with a compound of formula 3, e.g., under alkaline conditions, to give a compound of formula 4M;

the reaction scheme being as follows:

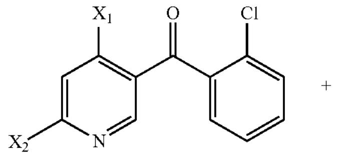

1

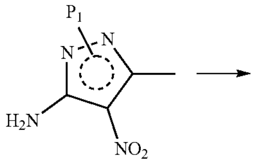

2M

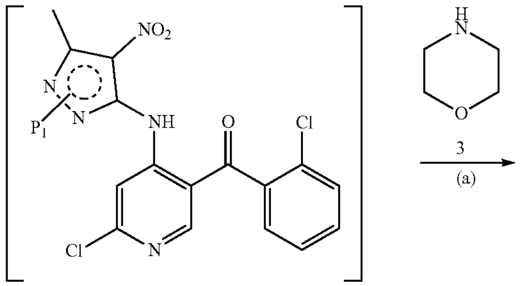

IM

-continued

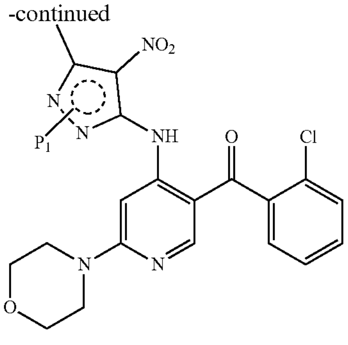

4M wherein $X_1$ and $X_2$ are each selected from halogen; $P_1$ is an amino-protecting group, and preferably, $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located;

6. the method according to any one of the preceding technical solutions, wherein in step (a), the organic solvent is selected from one or more of 2-methyltetrahydrofuran, acetonitrile, tetrahydrofuran and toluene; the base is selected from one or more of sodium hydride, sodium hydroxide, cesium carbonate, triethylene diamine, sodium tert-butoxide, potassium tert-butoxide, lithium bis(trimethylsilyl)amide and sodium hexamethyldisilazide;

optionally, in step (a), the reaction is performed at a pressure of 0 MPa to 10 MPa (gauge pressure), for example, atmospheric pressure;

the reaction is performed for a time period of 1-96 h, e.g., 17 h; the reaction is performed at a temperature that may be reflux temperature;

in particular, the aromatic nucleophilic substitution reaction of the compound of formula 1 with the compound of formula 2M under the action of the base is performed for a time period of 3-18 h, e.g., 3-8 h, at a temperature of 40° C. to 70° C., e.g., 40° C. to 60° C.;

in particular, the another aromatic nucleophilic substitution reaction with the compound of formula 3 is performed for a time period of 8 h to 16 h, e.g., 13 h to 16 h, at a temperature that may be reflux temperature;

a ratio is:

the solvent:the compound of formula 1:the compound of formula 2M:the compound of formula 3:the base=(0.5-60) L:(0.1-11) mol:1 mol:(0.3-30) mol:(0.2-25) mol, e.g., 5.8 L:1.1 mol:1 mol:3 mol:2.5 mol;

in particular, magnesium sulfate is added in the aromatic nucleophilic substitution reaction of the compound of formula 1 with the compound of formula 2M under the action of the base, and acetic acid is added in the another aromatic nucleophilic substitution reaction with the compound of formula 3, a ratio is:

the solvent:the compound of formula 1:the compound of formula 2M:the compound of formula 3:the base:magnesium sulfate:acetic acid=(0.5-60) L:(0.1-11) mol:1 mol:(0.3-30) mol:(0.2-25) mol:(0.2-20) mol:(0.1-15) mol, e.g., 5.8 L:1.1 mol:1 mol:3 mol:2.5 mol:1.6 mol:1.5 mol;

7. the method according to any one of the preceding technical solutions, wherein in step (b), the organic solvent is selected from one or more of methanol, ethanol, isopropanol, tetrahydrofuran, 2-methyltetrahydrofuran, acetic acid and acetonitrile; the catalyst is selected from iron powder, platinum oxide, Pt/C, $Pd(OH)_2/C$, Rh/C and Pd/C;

optionally, in step (b), when the catalyst is iron powder, the reaction is performed for a period of time of 1-96 h, e.g., 15-24 h, at a pressure of 0 MPa to 10 MPa (gauge pressure), e.g., atmospheric pressure, at a temperature that is reflux temperature;

a ratio is:

the organic solvent:the compound of formula 4M:the catalyst=(1-130) L:1 mol:(1-150) mol, e.g., 13 L:1 mol:(10-18) mol, e.g., 13 L:1 mol:(14-18) mol, e.g., 13 L:1 mol:15 mol;

in particular, when the catalyst is iron powder: in step (b), ammonium chloride is also added in an amount of 0.05-5 mol, e.g., 0.5 mol; the solvent is a mixed solvent of ethanol and tetrahydrofuran, e.g., in an ethanol-to-tetrahydrofuran volume ratio of (6-10):10;

in particular, in step (b), when the catalyst is platinum oxide, Pt/C, $Pd(OH)_2/C$, Rh/C or Pd/C, the reaction is performed in a hydrogen atmosphere at 30° C. to 80° C. for 20 to 80 h; for example, the reaction is performed in a hydrogen atmosphere at 60° C. to 80° C. for 20 to 72 h; the reaction is performed at a pressure greater than 0 MPa to 10 MPa (gauge pressure), e.g., 0.5-2 MPa; a ratio is: the solvent:the compound of formula 4M:the catalyst=(1-50) mL:1 g:(0.03-0.2) g, e.g., 22 mL:1 g:0.1 g;

optionally, in step (b), a small amount of water is also added; for example, a volume ratio of water to tetrahydrofuran is (0.2-2):10;

8. the method according to any one of the preceding technical solutions, wherein in step (c), the acid is selected from one or more of trifluoroacetic acid, methanesulfonic acid, p-toluenesulfonic acid, formic acid, acetic acid and hydrochloric acid; the organic solvent is selected from at least one of dichloromethane, methanol, ethanol and isopropanol;

optionally in step (c), the reaction is performed for a time period of 1-96 h, e.g., 1.5-3 h, at a pressure of 0 MPa to 10 MPa (gauge pressure), e.g., atmospheric pressure, at a temperature that is reflux temperature; a ratio is: the solvent:the compound of formula 5M:the acid=(0.5-70) L:1 mol:0.220 mol, e.g., 6.6 L:1 mol:2 mol;

9. the method according to any one of the preceding technical solutions, wherein specifically, step (c) is: allowing the compound of formula 5M to reflux in isopropanol under the action of trifluoroacetic acid for 1 h to 3 h;

10. the method according to any one of the preceding technical solutions, wherein in step (d), the organic solvent is selected from one or more of toluene, dichloromethane, acetonitrile, tetrahydrofuran, methanol, ethanol and isopropanol;

in step (d), an acid is also added, and the acid is selected from at least one of formic acid, acetic acid, hydrochloric acid, methanesulfonic acid and trifluoroacetic acid;

in step (d), in addition to the solvent, an alcohol or phenol is added; the alcohol is selected from methanol and/or ethanol, and the phenol is selected from phenol and/or p-methoxyphenol;

optionally in step (d), the reaction is performed for a time period of 1-96 h, e.g., 17 h, at a pressure of 0 MPa to 10 MPa (gauge pressure), e.g., atmospheric pressure, at a temperature that is reflux temperature; a ratio is: the solvent:the compound of formula 6M:the acid:the alcohol or phenol=(10-800) L:1 mol:(0.1-10) mol:(0.2-20) mol, e.g., 84 L:1 mol:1 mol:2 mol;

11. the method according to any one of the preceding technical solutions, further comprising steps of synthesizing the compound of formula 2M:

(i) subjecting a compound of formula 2-1 (e.g., 1 molar equivalent) to a nitration reaction with nitric acid (e.g., 1-2 molar equivalents) in a solvent such as concentrated sulfuric acid, acetic anhydride or acetic acid for a time period of 0.5-2 h at a temperature of 10-20° C. to give a compound of formula 2-2;

(ii) subjecting the compound of formula 2-2 (e.g., 1 molar equivalent) to an amino-protection reaction with an amino-protecting reagent (e.g., 1-1.5 molar equivalents) in an organic solvent such as one or more of tetrahydrofuran, 2-methyltetrahydrofuran, dichloromethane and acetonitrile for a time period of 1-48 h at a temperature of 60-100° C. to give a compound of formula (2-3)M; and (iii) subjecting the compound of formula (2-3)M (e.g., 1 molar equivalent) to a reaction in an organic solvent such as one or more of ethanol, tetrahydrofuran and acetonitrile, e.g., for a time period of 1-3 h at a temperature that is reflux temperature, to remove a phthaloyl group to give a compound of formula 2M;

the reaction scheme being as follows:

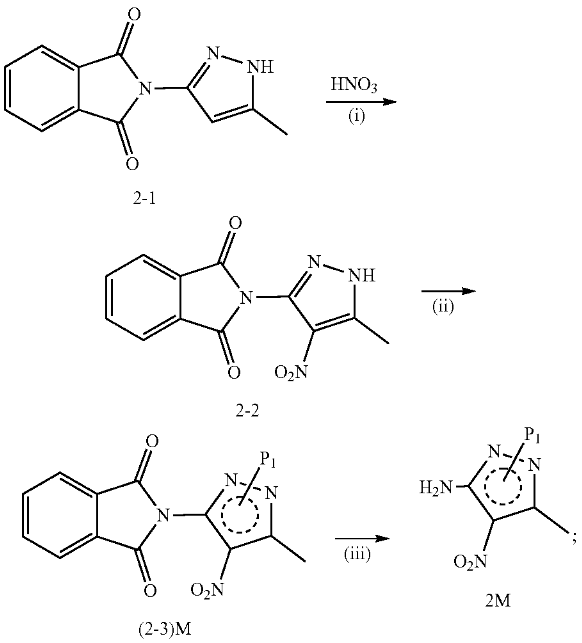

2-1

2-2

(2-3)M

2M wherein the amino-protecting reagent is $Boc_2O$, CbzCl, TosCl, FmocCl, PMBBr, MOMCl, EOMCl, tert-butanol, isobutylene, BnCl, acetic anhydride, SEMCl, TrtCl or DHP, e.g., $Boc_2O$, CbzCl, TosCl, FmocCl, PMBBr, TrtCl or DHP; $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located;

12. the method according to technical solution 11, wherein when the amino-protecting reagent is TrtCl, the reaction in step (ii) is performed under the following conditions: under the action of a base at 60° C. to 100° C. for 1 h to 48 h;

when the amino-protecting reagent is DHP, the reaction in step (ii) is performed under the following conditions: under the action of p-toluenesulfonic acid or pyridinium p-toluenesulfonate at 60° C. to 100° C. at reflux for 3 h to 48 h;

13. the method according to any one of the preceding technical solutions, further comprising a step of synthesizing the compound of formula 1:

subjecting a compound of formula 1-1 (e.g., 1-2 molar equivalents) to a coupling reaction with a compound of formula 1-2 (e.g., 1-2 molar equivalents) in an organic solvent such as THF for a time period of 2-4 h at a temperature of −70° C. to 60° C. to give the compound of formula 1;

the reaction scheme being as follows:

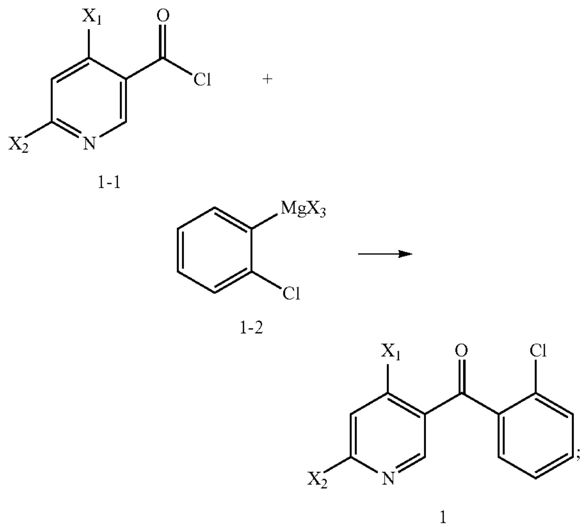

1-1 + 1-2 → 1 wherein $X_1$, $X_2$ and $X_3$ are each selected from halogen; preferably, $X_1$, $X_2$ and $X_3$ are each selected from chlorine;

14. an intermediate for preparing an anti-tumor compound of formula 7, having the following structural formulas:

1

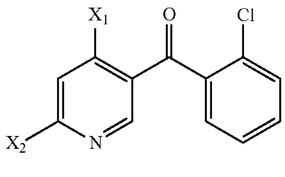

2M

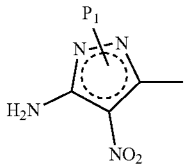

-continued

4M

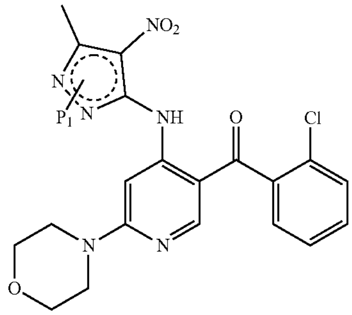

IM

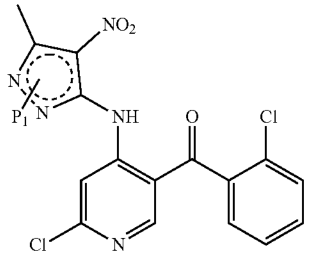

5M

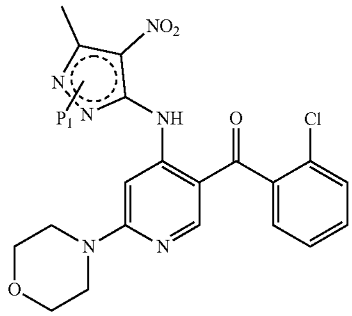

6M

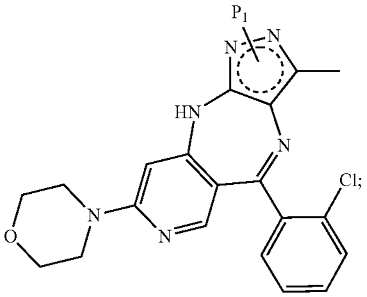

wherein, $X_1$ and $X_2$ are each independently selected from halogen;

$P_1$ is selected from Trt and THP; $P_1$ is linked to any N atom in a ring where $P_1$ is located, and preferably, $P_1$ is linked to a N atom ortho to a methyl group in the ring where $P_1$ is located; and 15. an intermediate for preparing an anti-tumor compound of formula 7, having the following structural formula:

6M

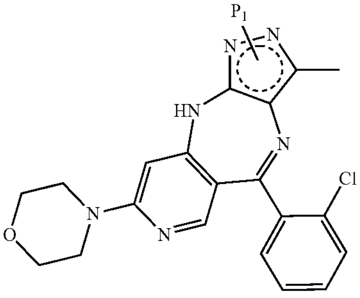

wherein $P_1$ is selected from Trt and THP; $P_1$ is linked to any N atom in a ring where $P_1$ is located, and preferably, $P_1$ is linked to a N atom ortho to a methyl group in the ring where $P_1$ is located;

the formula 6M is a complex comprising one molecule of trifluoroacetic acid and one molecule of isopropanol.

In a second aspect, the present invention is intended to provide a method for synthesizing an anti-tumor compound of formula 7, which comprises the following steps:

7

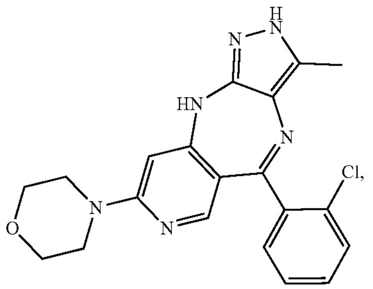

(a) subjecting a compound of formula 1 to an aromatic nucleophilic substitution reaction with a compound of formula 2 in an organic solvent under the action of a base, and then to another aromatic nucleophilic substitution reaction with a compound of formula 3, e.g., under alkaline conditions, to give a compound of formula 4;

(b) subjecting the compound of formula 4 to a reduction reaction in an organic solvent under the action of a catalyst to give a compound of formula 5;

(c) subjecting the compound of formula 5 to a ring-closing reaction in an organic solvent under the action of an acid to give a compound of formula 6; and (d) subjecting the compound of formula 6 to a reaction in an organic solvent to remove an amino-protecting group to give the anti-tumor compound of formula 7;

the reaction scheme being as follows:

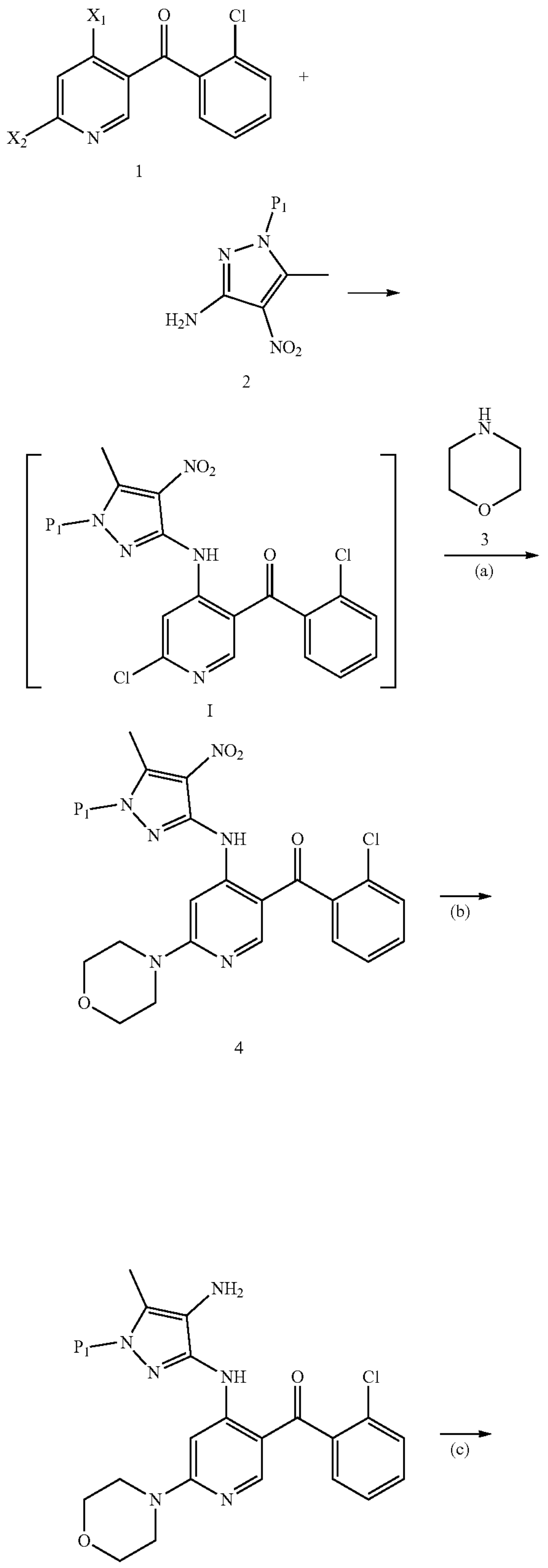

-continued

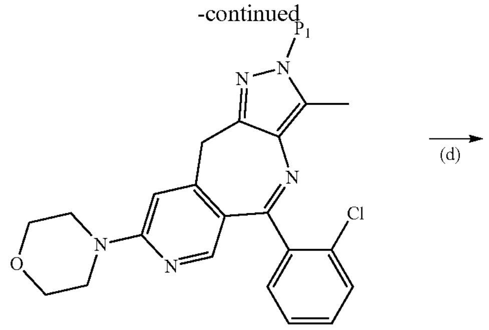

6

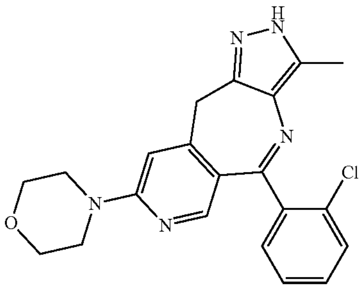

7 wherein, $X_1$ and $X_2$ are each independently selected from halogen; $P_1$ is an amino-protecting group selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP.

In one embodiment, in step (a), the organic solvent is selected from one or more of 2-methyltetrahydrofuran, acetonitrile, tetrahydrofuran and toluene; the base is selected from one or more of sodium hydride, sodium hydroxide, cesium carbonate, triethylene diamine, sodium tert-butoxide, potassium tert-butoxide, lithium bis(trimethylsilyl)amide and sodium hexamethyldisilazide.

In one embodiment, in step (b), the organic solvent is selected from one or more of methanol, ethanol, isopropanol, tetrahydrofuran, 2-methyltetrahydrofuran and acetonitrile; the catalyst is selected from iron powder, platinum oxide, Pt/C and Pd/C.

In one embodiment, in step (c), the acid is selected from one or more of trifluoroacetic acid, methanesulfonic acid, p-toluenesulfonic acid, formic acid, acetic acid and hydrochloric acid; the organic solvent is selected from at least one of dichloromethane, methanol, ethanol and isopropanol.

In one embodiment, specifically, step (c) is: allowing the compound of formula 5 to reflux in isopropanol under the action of trifluoroacetic acid for 1 h to 3 h, e.g., 1.5 h to 3 h.

In one embodiment, in step (d), the organic solvent is selected from one or more of toluene, dichloromethane, acetonitrile, tetrahydrofuran, methanol, ethanol and isopropanol;

in step (d), a catalyst is also added, and the catalyst is selected from at least one of formic acid, acetic acid, hydrochloric acid, methanesulfonic acid and trifluoroacetic acid;

in step (d), an alcohol or phenol is added; the alcohol is selected from methanol and/or ethanol, and the phenol is selected from phenol and/or p-methoxyphenol.

In one embodiment, further comprised are steps of synthesizing the compound of formula 2:

(i) subjecting a compound of formula 2-1 to a nitration reaction with nitric acid in a solvent to give a compound of formula 2-2;

(ii) subjecting the compound of formula 2-2 to an amino-protection reaction with an amino-protecting reagent in an organic solvent to give a compound of formula 2-3; and (iii) subjecting the compound of formula 2-3 to a reaction in an organic solvent to remove a phthaloyl group to give the compound of formula 2;

the reaction scheme being as follows:

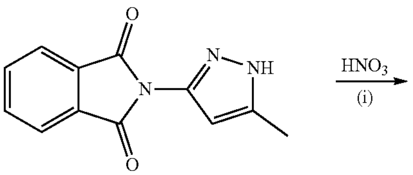

2-1

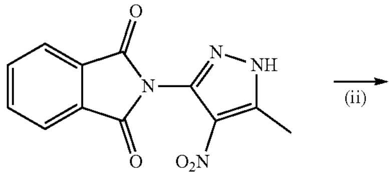

2-2

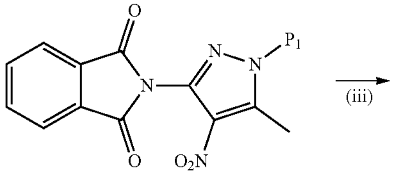

2-3

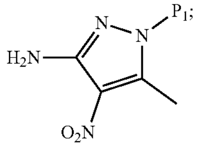

2 wherein the amino-protecting reagent is $Boc_2O$, CbzCl, TosCl, FmocCl, PMBBr, MOMCl, EOMCl, tert-butanol, isobutylene, BnCl, acetic anhydride, SEMCl, TrtCl or DHP, e.g., $Boc_2O$, CbzCl, TosCl, FmocCl, PMBBr, TrtCl or DHP; $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP.

In one embodiment, when the amino-protecting reagent is TrtCl, the reaction in step (ii) is performed under the following conditions: under the action of a base at 60° C. to 100° C. for 1 h to 48 h;

when the amino-protecting reagent is DHP, the reaction in step (ii) is performed under the following conditions: under the action of p-toluenesulfonic acid or pyridinium p-toluenesulfonate at 60° C. to 100° C. at reflux for 3 h to 48 h.

In one embodiment, further comprised are steps of synthesizing the compound of formula 1:

subjecting a compound of formula 1-1 to a coupling reaction with a compound of formula 1-2 in an organic solvent to give the compound of formula 1;

the reaction scheme being as follows:

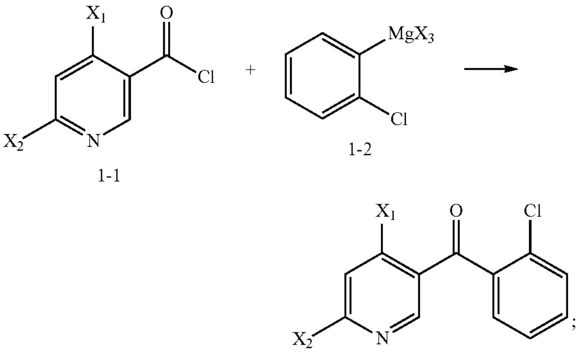

1-1

1-2

1 wherein $X_1$, $X_2$ and $X_3$ are each selected from halogen; preferably, $X_1$, $X_2$ and $X_3$ are each selected from chlorine;

In a third aspect, the present invention also provides an intermediate for preparing an anti-tumor compound of formula 7, which has the following structural formulas:

1

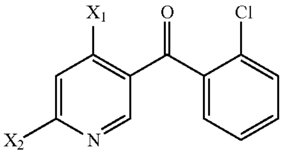

2A

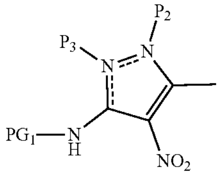

2

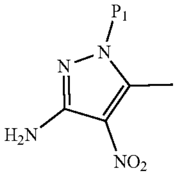

4

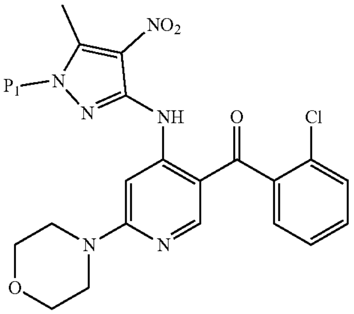

-continued

I

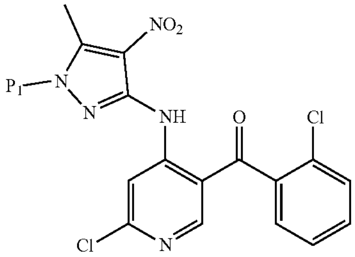

5

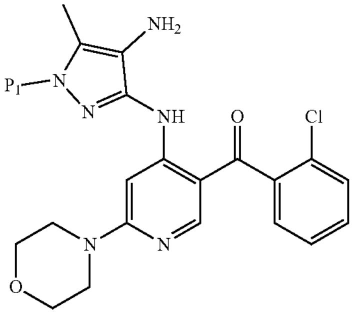

6

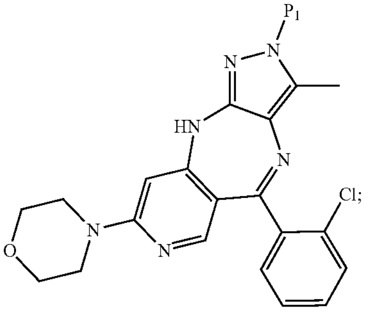

wherein, $X_1$ and $X_2$ are each independently selected from halogen;

$P_1$ is selected from Trt and THP;

$P_2$ is selected from Trt and THP, and $P_3$ is absent; or $P_3$ is selected from Trt and THP, and $P_2$ is absent;

$PG_1$ is acetyl, or $PG_1$-NH— is

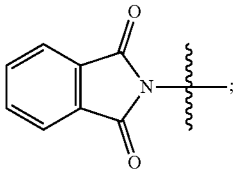

⚋ indicates a possible single bond or double bond.

In a fourth aspect, the present invention provides an intermediate for preparing an anti-tumor compound of formula 7, which has the following structural formula:

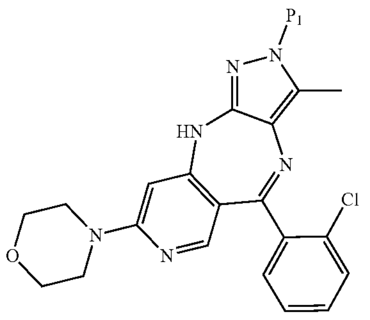

6 wherein $P_1$ is selected from Trt and THP;

the formula 6 is a complex comprising one molecule of trifluoroacetic acid and one molecule of isopropanol.

Compared with the prior art, the present invention has the beneficial effects described below.

(1) The present invention is different from the existing synthesis process where deprotection is prior to formation of a tricyclic ring in that a process where a tricyclic ring is synthesized prior to deprotection is adopted. In this process, an intermediate (the compound of formula 2) is used as a starting material and subjected to aromatic nucleophilic substitution reactions and a reduction reaction to give a compound of formula 5, through which the process where formation of a tricyclic ring is prior to deprotection can be achieved, thereby avoiding the disadvantages in the existing process that: a) in prior deprotection, a large amount of trifluoroacetic acid is needed and thus results in wastewater; b) in subsequent formation of a tricyclic ring, stannous chloride is used for reduction, leading to problems with operability and complicated workup; c) column chromatography is necessary for the process that is complicated as a whole.

(2) The synthesis method of the present invention has improved operability and allows for a simplified process, in which higher purity can be achieved without the complicated process of recrystallizing the synthesized compound of formula 7, and thus less of the three wastes is produced, making the method more suitable for industrial mass production.

(3) Where the intermediates according to the present invention are used for preparing an anti-tumor compound, by-products are effectively reduced during reactions, and thus the overall yield of the reactions are improved, and is at least twice as high as that obtained using the synthesis method for compound 29 in patent WO2018108079A1.

DETAILED DESCRIPTION

The above description of the present invention is explained in further detail by the following description of specific embodiments, but it should not be construed that the scope of the present invention is limited to the following examples. All techniques realized based on the above description of the present invention fall within the scope of the present invention.

The abbreviations used herein have the meanings commonly understood in the art as follows:

"Halogen" refers to fluorine, chlorine, bromine, iodine, etc.;
"$Boc_2O$" refers to di-tert-butyl dicarbonate;
"Boc" refers to tert-butyloxycarbonyl;
"CbzCl" refers to benzyl chloroformate;
"Cbz" refers to benzyloxycarbonyl;
"TosCl" refers to p-toluenesulfonyl chloride;
"Tos" refers to p-toluenesulfonyl;
"FmocCl" refers to 9-fluorenylmethyl chloroformate;
"Fmoc" refers to 9-fluorenylmethoxycarbonyl;
"PMBBr" refers to p-methoxybenzyl bromide;
"PMB" refers to p-methoxybenzyl;
"MOMCl" refers to chloromethyl methyl ether;
"MOM" refers to methoxymethyl;
"EOMCl" refers to chloromethyl ethyl ether;
"EOM" refers to ethoxymethyl;
"tBu" refers to tert-butyl;
"BnCl" refers to benzyl chloride;
"Bn" refers to benzyl;
"Ac" refers to acetyl;
"SEMCl" refers to 2-(trimethylsilyl)ethoxymethyl chloride;
"SEM" refers to 2-(trimethylsilyl)ethoxymethyl;
"TrtCl" refers to triphenylchloromethane;
"Trt" refers to triphenylmethyl;
"DHP" refers to 3,4-dihydro-2H-pyran;
"THP" refers to 2-tetrahydropyranyl;
"THF" refers to tetrahydrofuran;
"2-MeTHF" refers to dimethyl tetrahydrofuran;
"MTBE" refers to methyl tert-butyl ether;
"ACN" refers to acetonitrile;
"TEA" refers to triethylamine;
"TFA" refers to trifluoroacetic acid;
"IPA" refers to isopropanol;
"TEMPO" refers to 2,2,6,6-tetramethylpiperidine-1-oxide;
"DCM" refers to dichloromethane;
"TLC" refers to thin-layer chromatography;
"HNMR" refers to proton nuclear magnetic resonance spectroscopy;
"DMSO" refers to dimethyl sulfoxide;
"HPLC" refers to high performance liquid chromatography;
"PE" refers to petroleum ether;
"EA" refers to ethyl acetate;
"LC-MS" refers to liquid chromatography-mass spectrometry.

In the present invention, a catalyst includes substances capable of changing the reaction rate in conventional terms and also substances that serve redox or acid-base functions in the reaction.

In the present invention, a reaction is performed at atmospheric pressure unless otherwise specified.

In the present invention, a temperature at which a reaction is performed refers to the highest temperature that is reached in the reaction. The whole process of the reaction or a part of the process of the reaction is performed at that highest temperature.

In the present invention, when a "ratio" is referred to, for example, the solvent:the compound of formula 1:the compound of formula 2M:the compound of formula 3:the base=5.8 L:1.1 mol: 1 mol:3 mol:2.5 mol, such expression refers to a proportion relationship between the added amounts of the materials in reactions, that is, 1 mol of the compound of formula 2M is added, and correspondingly, the added amounts of the solvent, the compound of formula 1, the compound of formula 3 and the base are 5.8 L, 1.1 mol, 3 mol and 2.5 mol, respectively; if the added amount of the compound of formula 2M is increased or lowered, the added amounts of the other materials are increased or lowered proportionally. The added amount of each material refers to the total amount of that material added in reactions. For example, if a material is added in one batch, the added amount refers to the amount of that batch, and if a material is added in multiple batches, the added amount refers to the total amount of these multiple batches. The materials mentioned in the ratio can be added simultaneously or separately.

In the present invention, the chemical structural formula represents the compound of that formula in the form of a free base or free acid, or a hydrate, solvate, acid salt or base salt, or a combination thereof. For example, the formula A below may include a free base form of formula A as well as various complexes of formula A, e.g., a complex comprising one molecule of trifluoroacetic acid and one molecule of isopropanol (as shown in formula B below).

A

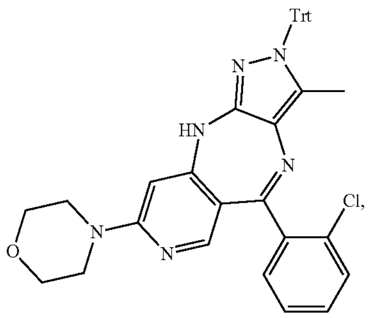

B

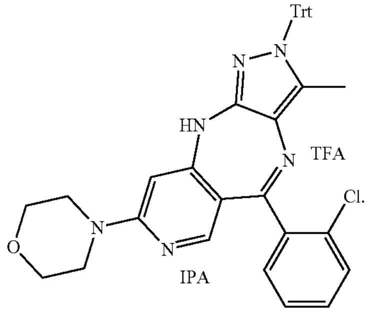

The present invention provides a method for synthesizing an anti-tumor compound of formula 7, which comprises the following steps:

7

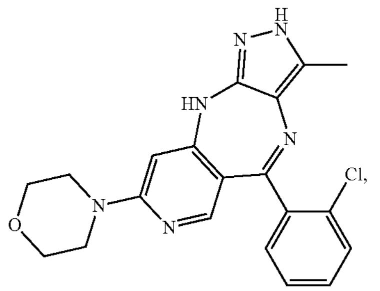

(a) subjecting a compound of formula 1 to an aromatic nucleophilic substitution reaction with a compound of formula 2M in an organic solvent under the action of a base to give a compound of formula IM, and subjecting the compound of formula IM separated or not separated to another aromatic nucleophilic substitution reaction with a compound of formula 3, e.g., under alkaline conditions, to give a compound of formula 4M;

(b) subjecting the compound of formula 4M to a reduction reaction in an organic solvent under the action of a catalyst to give a compound of formula 5M;

(c) subjecting the compound of formula 5M to a ring-closing reaction in an organic solvent under the action of an acid to give a compound of formula 6M; and (d) subjecting the compound of formula 6M to a reaction in an organic solvent to remove an amino-protecting group to give the anti-tumor compound of formula 7;

the reaction scheme being as follows:

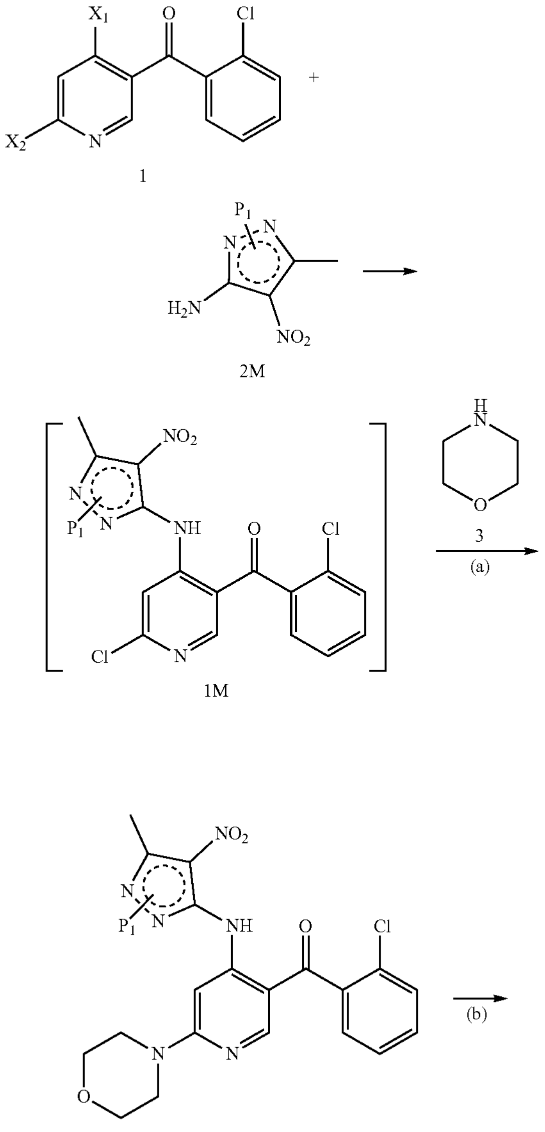

1

2M

1M

3

4M

-continued

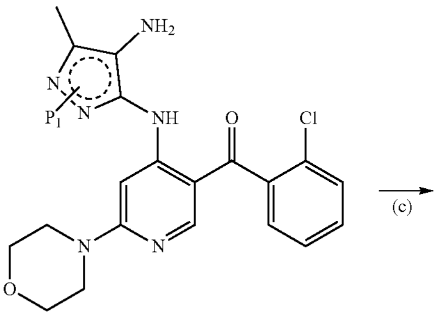

5M

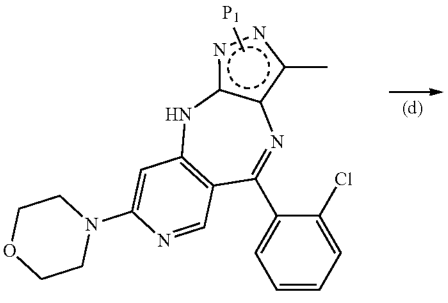

6M

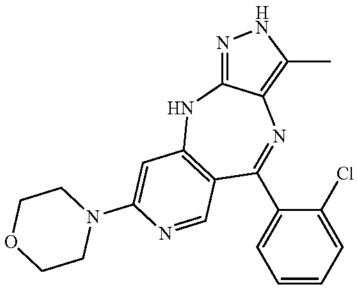

7 wherein $X_1$ and $X_2$ are each selected from halogen; $P_1$ is an amino-protecting group, and preferably, $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located.

In some embodiments, the compound of formula 2M includes a compound of formula 2 and a compound of formula 2m as shown below:

2

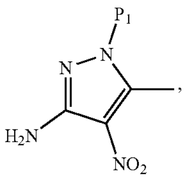

-continued

2m

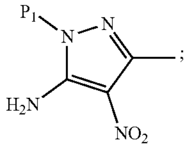

preferably, the compound of formula 2M is the compound of formula 2.

The compound of formula IM includes a compound of formula I and a compound of formula Im as shown below:

1

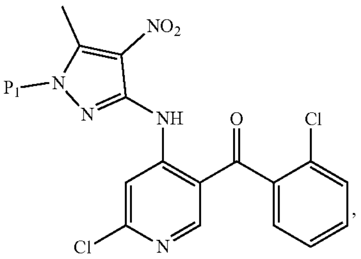

1m

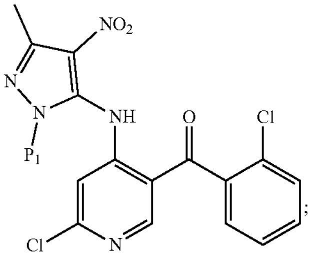

preferably, the compound of formula IM is the compounds of formula I.

The compound of formula 4M includes a compound of formula 4 and a compound of formula 4m as shown below:

4

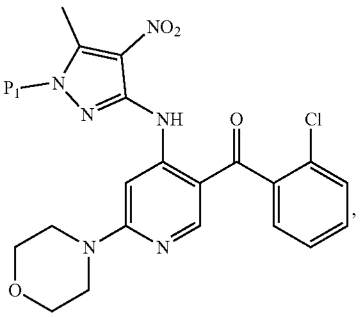

-continued

4m

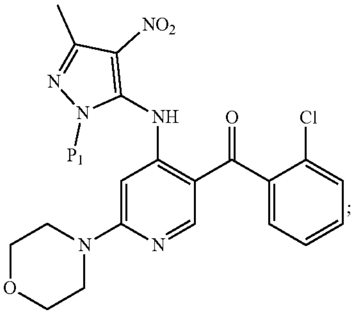

preferably, the compound of formula 4M is the compound of formula 4.

The compound of formula 5M includes a compound of formula 5 and a compound of formula 5m as shown below:

5

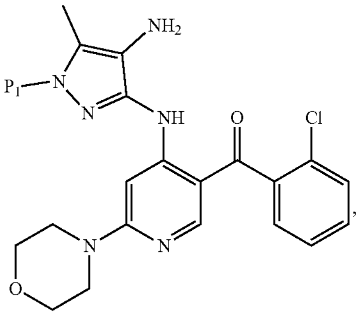

5m

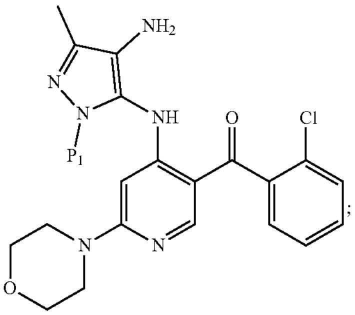

preferably, the compound of formula 5M is the compound of formula 5.

The compound of formula 6M includes a compound of formula 6 and a compound of formula 6m as shown below:

6

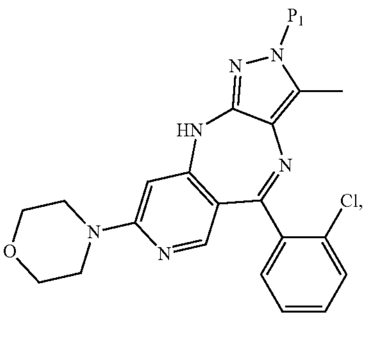

-continued

6m

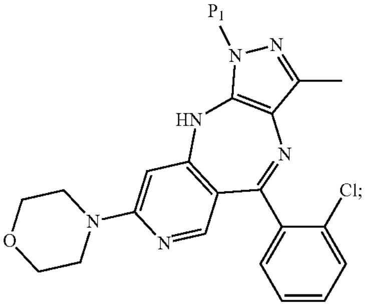

preferably, the compound of formula 6M is the compound of formula 6.

Preferably, $P_1$ is selected from Trt and THP.

In some embodiments, a method for synthesizing the compound of formula 4 is step (a): subjecting a compound of formula 1 to an aromatic nucleophilic substitution reaction with a compound of formula 2 in an organic solvent under the action of a base to give a compound of formula I, and subjecting the compound of formula IM not separated to another aromatic nucleophilic substitution reaction with a compound of formula 3, e.g., under alkaline conditions, to give a compound of formula 4.

In the present invention, in synthesizing the compound of formula 4, the product I of the reaction of the compound of formula 1 with the compound of formula 2 need not to be separated but is directly subjected to a reaction with the compound of formula 3, so the process is simplified and the yield is improved.

In some embodiments, in step (a), the organic solvent is selected from one or more of 2-methyltetrahydrofuran, acetonitrile, tetrahydrofuran and toluene.

Preferably, the organic solvent is selected from 2-methyltetrahydrofuran and acetonitrile.

In some embodiments, in step (a), the base is selected from one or more of sodium hydride, sodium hydroxide, cesium carbonate, triethylene diamine, sodium tert-butoxide, potassium tert-butoxide, lithium bis(trimethylsilyl)amide and sodium hexamethyldisilazide.

In some embodiments, to provide the alkaline conditions in step (a), morpholine can be used as a base instead of adding an additional base, or an additional basic reagent such as one or more of sodium hydride, sodium hydroxide, cesium carbonate, triethylene diamine, sodium tert-butoxide, potassium tert-butoxide, lithium bis(trimethylsilyl)amide and sodium hexamethyldisilazide can be added. In some embodiments, in step (a), the base is sodium hydride, and the solvent is 2-methyltetrahydrofuran.

In some embodiments, in step (a), the aromatic nucleophilic substitution reaction of the compound of formula 1 with the compound of formula 2 is performed under the following conditions: at 40° C. to 70° C. for 3 h to 18 h, e.g., at 40° C. to 60° C. for 3 h to 8 h.

In some embodiments, in step (a), the another aromatic nucleophilic substitution reaction with the compound of formula 3 is performed under the following conditions: at reflux for 8 h to 16 h, e.g., at reflux for 8 h to 12 h, or e.g., at reflux for 13 h to 16 h.

In some embodiments, in step (a), a molar ratio of the compound of formula 1 to the compound of formula 2 to the compound of formula 3 is (1-1.2):1:3.

In some embodiments, in step (a), magnesium sulfate, a molecular sieve or activated carbon may also be added as a catalyst.

In particular, magnesium sulfate is added as a catalyst in an amount of 0.2 to 3 molar equivalents of the compound of formula 2, e.g., 2 to 3 molar equivalents of the compound of formula 2, or e.g., 1 to 3 molar equivalents of the compound of formula 2.

Further, after the reaction in step (a) is completed, the compound of formula 4 is purified, and the purification can be performed using a conventional method in the art.

The present invention also provides another method for synthesizing the compound of formula 4, which comprises the following steps:

subjecting a compound of formula 1 to an aromatic nucleophilic substitution reaction with a compound of formula 2 in an organic solvent under the action of a base to give a compound of formula I; and subjecting the compound of formula I to an aromatic nucleophilic substitution reaction with the above compound of formula 3 in an organic solvent under the action of a base to give the compound of formula 4;

the reaction scheme being as follows:

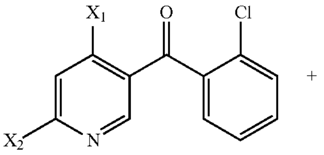

1

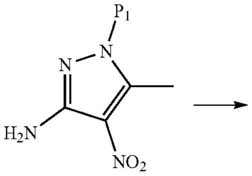

2

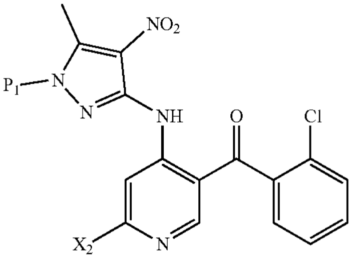

I

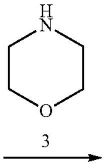

3

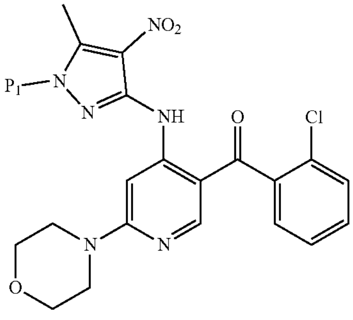

4 wherein, $X_1$ and $X_2$ are each independently selected from halogen; $P_1$ is an amino-protecting group preferably selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP.

In the method, the organic solvent is selected from one or more of 2-methyltetrahydrofuran, acetonitrile, tetrahydrofuran and toluene. The base is selected from one or more of sodium hydride, sodium hydroxide, cesium carbonate, triethylene diamine, sodium tert-butoxide, potassium tert-butoxide, lithium bis(trimethylsilyl)amide and sodium hexamethyldisilazide.

In some embodiments, steps of synthesizing the compound of formula 4m and reaction conditions are as described in the above method for synthesizing the compound of formula 4 except that the compound of formula 2m is used in place of the compound of formula 2 and the compound of formula Im in place of the compound of formula I.

In some embodiments, a method for synthesizing the compound of formula 5 is step (b): subjecting the compound of formula 4 to a reduction reaction in an organic solvent under the action of a catalyst to give a compound of formula 5.

In some embodiments, in step (b), the organic solvent is selected from one or more of methanol, ethanol, isopropanol, tetrahydrofuran, 2-methyltetrahydrofuran, acetic acid and acetonitrile.

In some embodiments, in step (b), the catalyst is selected from iron powder, platinum oxide, Pt/C, $Pd(OH)_2/C$, Rh/C and Pd/C.

In some embodiments, a mass fraction of Pt/C and Rh/C is 5%; a mass fraction of Pd/C is 5% or 10%; a mass fraction of $Pd(OH)_2/C$ is 10% or 20%.

When the catalyst is iron powder, iron powder is added in an amount of 10 to 18 molar equivalents, e.g., 14 to 18 molar equivalents, of the compound of formula 4.

In particular, in step (b), ammonium chloride is also added in an amount of 0.4 to 0.6 molar equivalents of the compound of formula 4; the solvent is a mixed solvent of ethanol and tetrahydrofuran, e.g., in an ethanol-to-tetrahydrofuran volume ratio of (6-10):10. In particular, in step (b), a small amount of water is also added, and a volume ratio of water to tetrahydrofuran is (0.2-0.5):10. Further, the reduction reaction is performed under the following conditions: at reflux for 15 h to 24 h.

When the catalyst is platinum oxide, the reduction reaction is performed under the following conditions: in a hydrogen atmosphere (e.g., at 0.5-0.8 MPa) at 35° C. to 80° C. for 20 h to 70 h. For example, the reduction reaction is performed under the following conditions: in a hydrogen atmosphere at 35° C. to 50° C. for 40 h to 50 h.

Further, after the reaction in step (b) is completed, the compound of formula 5 is purified, and the purification can be performed using a conventional method in the art.

In some embodiments, steps of synthesizing the compound of formula 5m and reaction conditions are as described in the above method for synthesizing the compound of formula 5 except that the compound of formula 4m is used in place of the compound of formula 4.

In some embodiments, a method for synthesizing the compound of formula 6 is step (c): subjecting the compound of formula 5 to a ring-closing reaction in an organic solvent under the action of an acid to give a compound of formula 6.

In some embodiments, in step (c), the acid is selected from one or more of trifluoroacetic acid, methanesulfonic acid, p-toluenesulfonic acid, formic acid, acetic acid and hydrochloric acid. The organic solvent is selected from at least one of dichloromethane, methanol, ethanol and isopropanol.

In particular, the acid is selected from trifluoroacetic acid, and the organic solvent is isopropanol.

In some embodiments, in step (c), an amount-of-substance ratio of the compound of formula 5 to the acid is 1:(1.5-2).

In some embodiments, specifically, step (c) is: allowing the compound of formula 5 to reflux in isopropanol under the action of trifluoroacetic acid for 1 h to 3 h, e.g., for a time period of 1.5 h to 3 h.

Further, after the reaction in step (c) is completed, the compound of formula 6 is purified, that is, the reaction mixture is filtered under vacuum, and the filter cake is rinsed with isopropanol and dried to give a purified compound of formula 6.

In some embodiments, steps of synthesizing the compound of formula 6m and reaction conditions are as described in the above method for synthesizing the compound of formula 6 except that the compound of formula 5m is used in place of the compound of formula 5.

In some embodiments, a method for synthesizing the compound of formula 7 is step (d): subjecting the compound of formula 6 to a reaction in an organic solvent to remove an amino-protecting group to give the anti-tumor compound of formula 7.

In some embodiments, in step (d), the organic solvent is selected from one or more of toluene, dichloromethane, acetonitrile, tetrahydrofuran, methanol, ethanol and isopropanol. In particular, the organic solvent is toluene.

In some embodiments, in step (d), a catalyst is may also be added, and the catalyst is selected from at least one of formic acid, acetic acid, hydrochloric acid, methanesulfonic acid and trifluoroacetic acid. In particular, the catalyst is selected from trifluoroacetic acid.

Further, in step (d), an alcohol or phenol is added; the alcohol is selected from methanol and/or ethanol, and the phenol is selected from phenol and/or p-methoxyphenol. Further, for example, the alcohol or phenol is added in an amount of 1 to 2 molar equivalents of the compound of formula 6.

Further, after the reaction in step (d) is completed, the compound of formula 7 is purified, and the purification can be performed using a conventional method in the art.

In some embodiments, a step of synthesizing the compound of formula 7 by using the compound of formula 6m in place of the compound of formula 6 and reaction conditions are as described in the above method for synthesizing the compound of formula 7.

In some embodiments, the compound of formula 7 may also be synthesized directly from the compound of formula 5M in one step. The reaction is performed under the following conditions: subjecting the compound of formula 5M to a reaction in an organic solvent under the action of an acid to give the compound of formula 7. For example, the reaction is performed at reflux under the action of trifluoroacetic acid for 20-40 h. The organic solvent is selected from one or more of toluene, dichloromethane, acetonitrile, 2-methyltetrahydrofuran, tetrahydrofuran, methanol, ethanol and isopropanol.

In some embodiments, the method for synthesizing the anti-tumor compound of formula 7 further comprises steps of synthesizing the compound of formula 2M:

(i) subjecting a compound of formula 2-1 to a nitration reaction with nitric acid in a solvent to give a compound of formula 2-2;

(ii) subjecting the compound of formula 2-2 to an amino-protection reaction with an amino-protecting reagent in an organic solvent to give a compound of formula (2-3)M; and (iii) subjecting the compound of formula (2-3)M to a reaction in an organic solvent to remove a phthaloyl group to give the compound of formula 2M;

the reaction scheme being as follows:

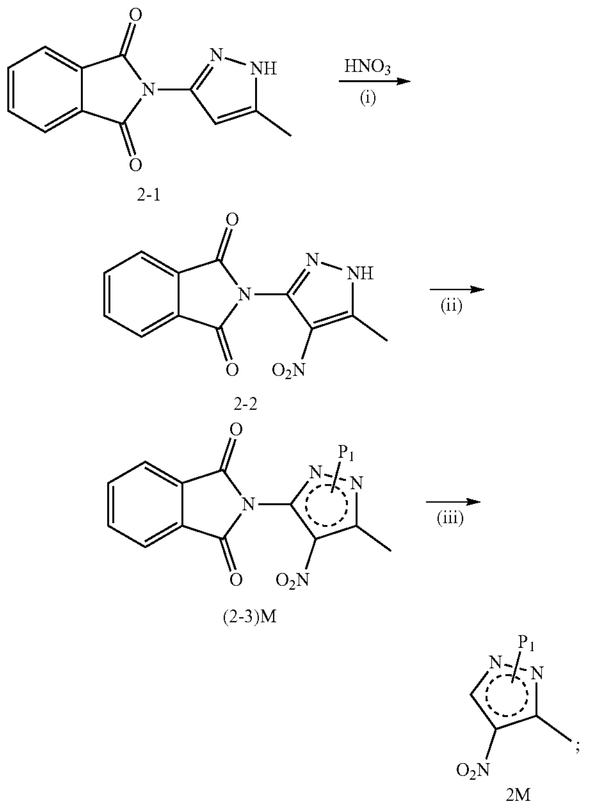

2-1
2-2
(2-3)M
2M wherein the amino-protecting reagent is $Boc_2O$, CbzCl, TosCl, FmocCl, PMBBr, MOMCl, EOMCl, tert-butanol, isobutylene, BnCl, acetic anhydride, SEMCl, TrtCl or DHP, e.g., $Boc_2O$, CbzCl, TosCl, FmocCl, PMBBr, TrtCl or DHP; $P_1$ is selected from Boc, Cbz, Tos, Fmoc, PMB, MOM, EOM, tBu, Bn, Ac, SEM, Trt and THP, e.g., Boc, Cbz, Tos, Fmoc, PMB, Trt and THP; $P_1$ is linked to any N atom in a ring where $P_1$ is located, and preferably, $P_1$ is linked to a N atom ortho to a methyl group in the ring where $P_1$ is located. Preferably, the amino-protecting reagent is TrtCl or DHP; $P_1$ is selected from Trt and THP.

In some embodiments, the compound of formula (2-3)M includes a compound of formula 2-3 and a compound of formula (2-3)m as shown below:

2-3

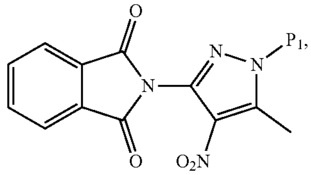

-continued (2-3)m

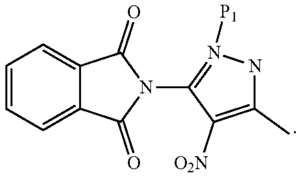

In some embodiments, the solvent in step (i) is, e.g., concentrated sulfuric acid, acetic anhydride or acetic acid.

In some embodiments, the nitration reaction in step (i) is performed under the following conditions: in concentrated sulfuric acid at 10° C. to 20° C. for 0.5 h to 2 h.

Further, a mass-to-volume ratio of the compound of formula 2-1 to concentrated sulfuric acid is 100 g:(150-250) mL.

Further, after the nitration reaction is completed, the resulting compound of formula 2-2 is easy to filter and has good solubility in solvents such as tetrahydrofuran, dichloromethane, acetonitrile, etc., so the selection of reaction solvents is more diversified.

In some embodiments, in step (ii), different reaction conditions are set depending on the nature of the amino-protecting reagent. In particular, when the amino-protecting reagent is TrtCl, the reaction in step (ii) is performed under the following conditions: under the action of a base at 60° C. to 100° C. for 1 h to 48 h; when the amino-protecting reagent is DHP, the reaction in step (ii) is performed under the following conditions: under the action of p-toluenesulfonic acid or pyridinium p-toluenesulfonate at 60° C. to 100° C. at reflux for 3 h to 48 h.

In some embodiments, the organic solvent for the reaction in step (ii) is selected from one or more of tetrahydrofuran, 2-methyltetrahydrofuran, dichloromethane and acetonitrile.

In particular, when the amino-protecting reagent is TrtCl, the reaction in step (ii) is performed under the following conditions: under the catalysis of triethylamine in acetonitrile at reflux for 1 h to 3 h.

In some embodiments, the reaction for removing the phthaloyl group in step (iii) is performed under the following conditions: under the action of hydrazine hydrate in an organic solvent at reflux for 1 h to 3 h, the organic solvent being selected from one or more of ethanol, tetrahydrofuran and acetonitrile.

In some embodiments, the method for synthesizing the anti-tumor compound of formula 7 further comprises a step of synthesizing the compound of formula 1:

subjecting a compound of formula 1-1 to a coupling reaction with a compound of formula 1-2 in an organic solvent to give the compound of formula 1;

the reaction scheme being as follows:

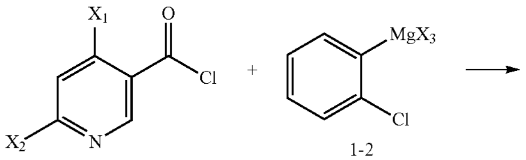

1-1 1-2

-continued

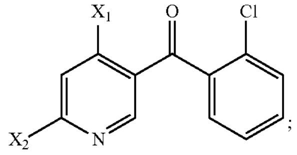

1 wherein $X_1$, $X_2$ and $X_3$ are each selected from halogen. Preferably, $X_1$, $X_2$ and $X_3$ are each selected from chlorine.

Further, the coupling reaction of the compound of formula 1-1 with the compound of formula 1-2 is performed under the following conditions: under the action of ferric acetylacetonate at −70° C. to −60° C.

The present invention also provides an intermediate for preparing an anti-tumor compounds of formula 7, which has the following structural formulas:

1

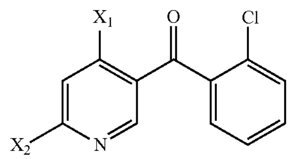

2M

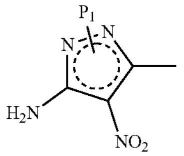

4M

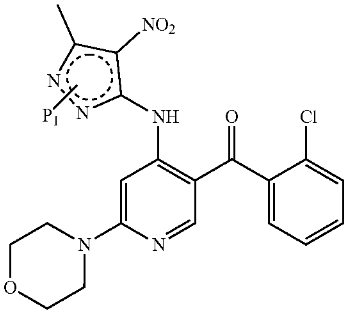

IM

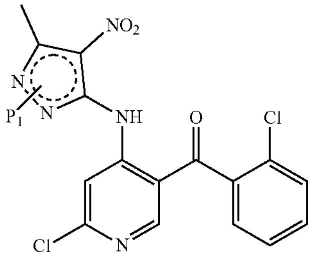

-continued

5M

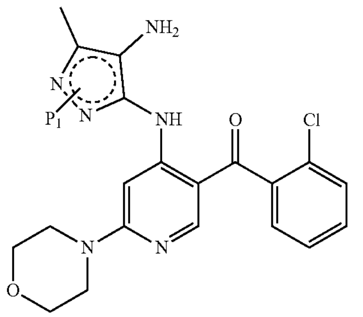

6M

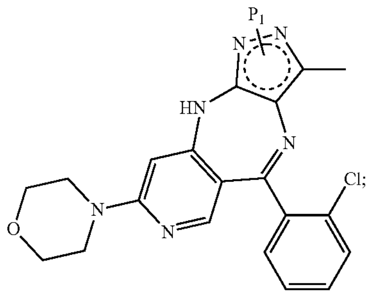

Preferably, the intermediate is of the following structures:

1

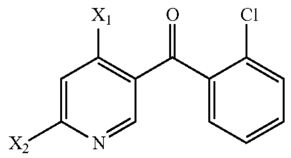

2

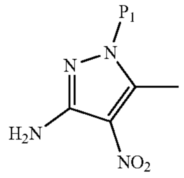

4

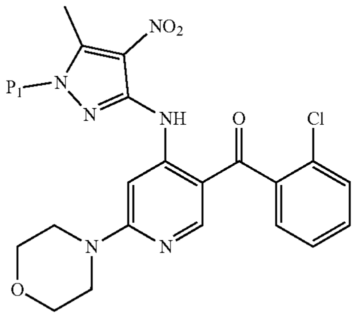

-continued

1

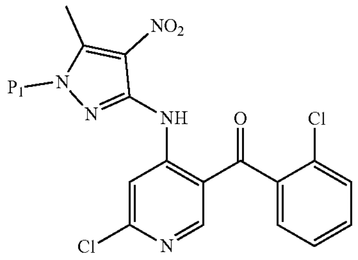

5

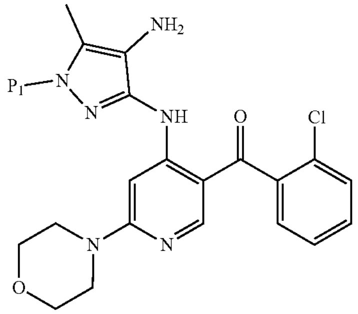

6

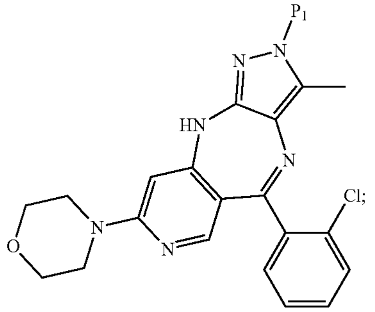

wherein, $X_1$ and $X_2$ are each independently selected from halogen;

wherein $P_1$ is selected from Trt and THP; $P_1$ is linked to any N atom in a ring where $P_1$ is located, and preferably, $P_1$ is linked to a N atom ortho to a methyl group in the ring where $P_1$ is located.

The present invention also provides an intermediate for preparing an anti-tumor compound of formula 7, which has the following structural formula:

6M

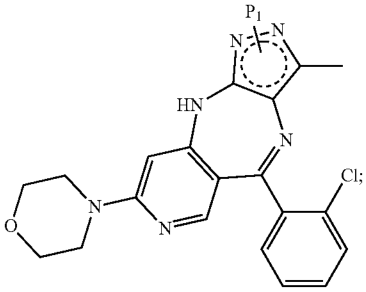

preferably the following structure:

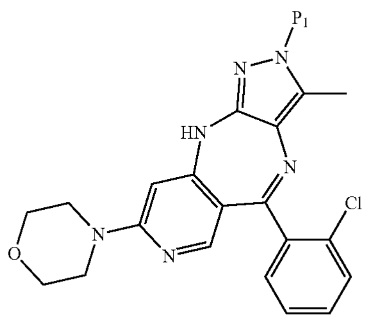

wherein $P_1$ is selected from Trt and THP;

the formula 6M is a complex comprising one molecule of trifluoroacetic acid and one molecule of isopropanol.

The present invention is further illustrated by the following description of examples, but the protection scope of the present invention is not limited thereto.

The starting materials used in the examples of the present invention are all commercially available products with chemical purity.

Example 1

Synthesis of Compound of Formula 1'

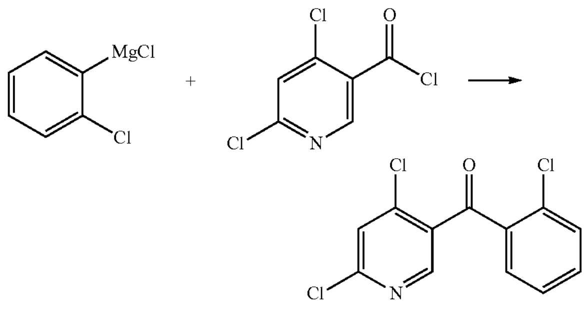

1'

Preparation of a solution of (2-chlorophenyl)magnesium chloride in THF: a solution of (2-chlorophenyl)magnesium chloride (27.34 mol) was prepared in THF (50.44 L, 0.542 M) and kept at −5° C. to 5° C. in the absence of oxygen for later use.

Preparation of a solution of 4,6-dichloronicotinoyl chloride in THF: 4,6-dichloronicotinoyl chloride (3.85 kg, 18.32 mol) was added to THF (25.0 L) and ferric acetylacetonate (193.16 g, 0.55 mol, 0.03 eq) to prepare a solution (28.0 L, 0.651 M) for later use.

Preparation of dilute hydrochloric acid: to a 100 L reactor were added 2.8 L of concentrated hydrochloric acid and 5.6 L of water, and the temperature was controlled at 5° C. to 15° C.; the prepared solution was for quenching.

In a micro-reactor set at a temperature of −70° C. to −60° C., the solution of (2-chlorphenyl)magnesium chloride in THF was subjected to a reaction with the solution of 4,6-dichloronicotinoyl chloride in THF to give (2-chlorphenyl)(4,6-dichloropyridin-3-yl)methanone in the reaction mixture. The reaction mixture was quenched by being introduced into the prepared dilute hydrochloric acid. The yellow clear organic phase was separated and concentrated. MTBE (17.5 L) was added to the concentration residue, and the organic phase was separated, concentrated to remove the solvent, and then added to 2 L of n-heptane to give a brownish-yellow crude product. The crude product was added to 3.3 L of ethanol and 9.9 L of n-heptane, and the mixture was heated to 60° C., cooled to 5° C. to 10° C. after the crude product was completely dissolved, and filtered. The filter cake was dried to give a pale yellow powder (2.78 kg, 53.3% yield).

$^1$HNMR (400 MHz, DMSO-d6) δ (ppm): 8.61-8.57 (m, 1H), 8.02 (s, 1H), 7.70-7.62 (m, 3H), 7.55-7.51 (m, 1H).

Synthesis of Compound of Formula 1"

Step 1: Synthesis of (6-bromopyridin-3-yl)(2-chlorophenyl)methanol

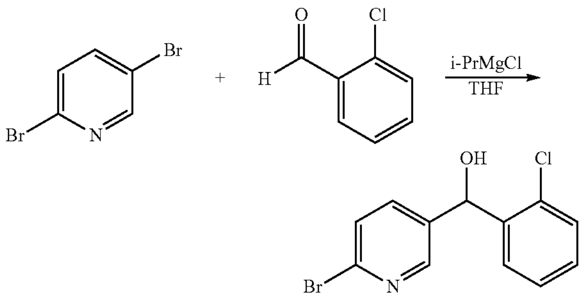

To a 2 L four-necked flask were added anhydrous tetrahydrofuran (500 mL) and 2,5-dibromopyridine (100.0 g, 0.42 mol, 1.0 eq), and the mixture was cooled under stirring in an ice-water bath to 2° C. Isopropyl magnesium chloride (210.5 mL, 2.0 M, 0.42 mol, 1.0 eq) was added dropwise over about 0.5 h with the temperature controlled to not exceed 10° C. The mixture was stirred at room temperature (20° C.) for 1 h and then cooled in an ice-water bath to 10° C., and a solution of 2-chlorobenzaldehyde (62.3 g, 0.443 mol, 1.05 eq) in tetrahydrofuran (200 mL) was added dropwise over about 0.5 h. The mixture was stirred at 10° C. for 2 h, and the reaction was completed as indicated by TLC. A saturated aqueous ammonium chloride solution (300 mL) was added to the reaction system. The mixture was stirred for 10 min, and then the organic phase was separated and concentrated to give a yellow oil. The aqueous phase was extracted with ethyl acetate (1.0 L×2), and the extracts were combined with the yellow oil previously obtained, washed with water (500 mL) and saturated brine (500 mL), dried over anhydrous $Na_2SO_4$, and concentrated to give a brown oil (140 g, crude).

Step 2: Synthesis of (6-bromopyridin-3-yl)(2-chlorophenyl)methanone

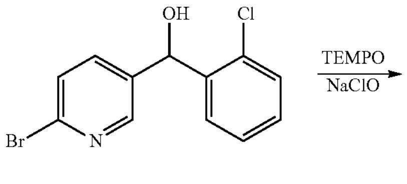

-continued

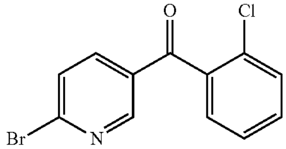

(6-Bromopyridin-3-yl)(2-chlorophenyl)methanol (140 g, crude) was dissolved in DCM (1.3 L), and TEMPO (1.51 g, 9.4 mmol) and NaBr (1.92 g, 18.8 mmol) were added. The mixture was cooled in an ice-water bath to 3° C., and an aqueous NaClO solution (1.34 mol/L, 600 L, 0.71 mol) neutralized by $NaHCO_3$ (45.0 g) was added dropwise, during which the temperature did not exceed 20° C. After dropwise addition, the mixture was stirred for 10 min, and the reaction was completed as indicated by TLC. The aqueous phase was separated and extracted with DCM (1.0 L), and the organic phases were combined, washed with water (1.0 L) and saturated brine (1.0 L), dried over anhydrous $Na_2SO_4$, and concentrated to give a yellow oil. The crude product was slurried with 150 mL of methyl tert-butyl ether/500 mL of petroleum ether to give a yellow solid (50.3 g, 39.7% yield over two steps).

Step 3: Synthesis of (6-bromo-4-iodo-pyridin-3-yl)(2-chlorophenyl)methanone

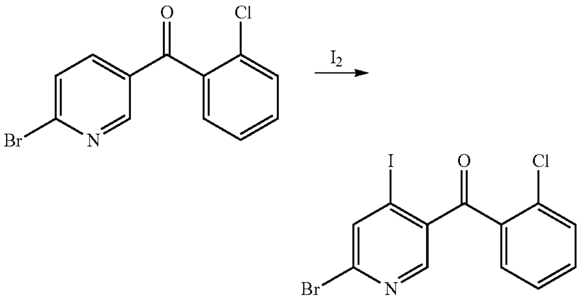

1″

In nitrogen atmosphere, a solution of tetramethylpiperidine lithium/magnesium chloride (281 mL, 1.5 mol/L, 0.43 mol, 2.5 eq) was added to a 2 L four-necked flask and cooled in a dry ice/ethanol bath to −65° C., and a solution of (6-bromopyridin-3-yl)(2-chlorophenyl)methanone (50.0 g, 0.17 mol, 1.0 eq) in tetrahydrofuran (50 mL) was added dropwise over about 0.5 h. Then the mixture was warmed to −45° C., stirred for 1 h, and then cooled to −65° C., and a solution of 12 (129.3 g, 0.51 mol, 3.0 eq) in tetrahydrofuran (400 mL) was added dropwise over about 1 h. The mixture was stirred for 20 min, and then the reaction was completed as indicated by TLC. To the reaction system were added a saturated aqueous ammonium chloride solution (500 mL) and a saturated aqueous $NaHSO_3$ solution (500 mL). The mixture was stirred for 15 min and filtered, and the insoluble matter was washed with ethyl acetate (500 mL×2). The filtrates were combined, and the aqueous phase was separated and extracted with ethyl acetate (1.0 L×2). All the organic phases were combined, washed with water (800 mL) and saturated brine (800 mL), dried over anhydrous $Na_2SO_4$, and concentrated to give a yellow solid. The solid was slurried with methyl tert-butyl ether (500 mL)/petroleum ether (500 mL) and dried to give a yellow solid (30 g, 41.8% yield).

Example 2

Synthesis of Compound 2'

Step 1: Synthesis of Compound of Formula 2-2

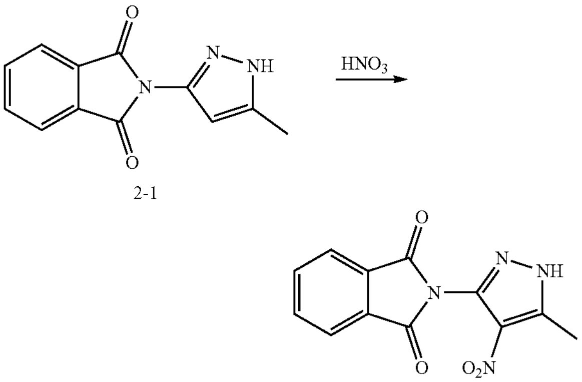

2-2

Concentrated sulfuric acid (7.5 L) was added to a four-necked flask and mixed well by stirring, and the system was cooled in an ice-water bath to below 20° C. The compound of formula 2-1 (3590 g, 15.80 mol, 1.0 eq) was added in batches. With the temperature of the system controlled at 10° C. to 20° C., 63% (mass fraction) concentrated nitric acid (1896.4 g, 18.96 mol, 1.2 eq) was added dropwise and slowly to the reaction system. After dropwise addition, the ice-water bath was removed, and the reaction system was allowed to react at 10° C. to 20° C. for 1 h. The starting materials were completely converted as indicated by TLC (DCM:MeOH=20:1). The reaction mixture was slowly poured into 36 kg ice water, and the resulting mixture was filtered under vacuum to dryness. Then the filter cake was added to a 50 L wide-mouth drum, followed by the addition of 36 L of water. The resulting mixture was stirred for 0.5 h and filtered under vacuum, and the filter cake was rinsed with water (6 L). The filter cake was dried to a constant weight (about 72 h) to give the compound of formula 2-2 as an off-white solid (4160 g, 96.7% yield, 95.5% HPLC purity).

$^1$HNMR (400 MHz, DMSO-d6) δ (ppm): 14.23 (br, 1H), 8.08-7.97 (m, 4H), 2.64 (s, 3H).

Step 2: Synthesis of Compound of Formula 2-3'

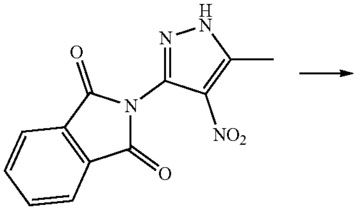

2-2

-continued

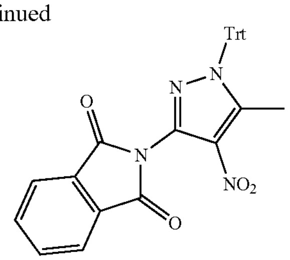

2-3'

To a reactor was added ACN (38 L), followed by the compound of formula 2-2 (4140 g, 15.21 mol, 1.0 eq) and TEA (1847 g, 18.25 mol, 1.2 eq) under stirring. The mixture was well mixed, and triphenylchloromethane (4664 g, 16.73 mol, 1.1 eq) was added. The system was heated at reflux (82° C.) for 2 h, and the reaction was completed. The system was cooled to 25° C. and filtered under vacuum, and the filter cake was rinsed twice with ACN (4 L×2). After being drained, the filter cake was slurried with 30 L of water for 2 h, followed by filtration under vacuum, and the filter cake was rinsed twice with water (4 L×2). After being drained, the filter cake was dried in a forced air drying oven at 50° C. for 24 h to give the compound of formula 2-3' as a white solid (6920 g, 99.7% HPLC purity, 88.4% yield).

$^1$HNMR (400 MHz, $CDCl_3$) δ(ppm): 7.97-7.92 (m, 2H), 7.82-7.78 (m, 2H), 7.41-7.33 (m, 9H), 7.22-7.19 (m, 6H), 2.08 (s, 3H).

Step 3: Synthesis of Compound of Formula 2'

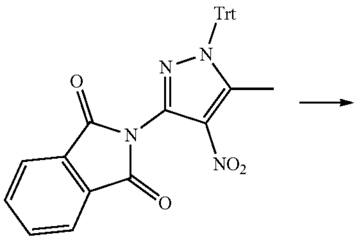

2-3'

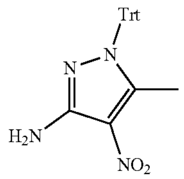

2'

THF (55 L) was equally divided into four 20 L four-necked flasks, and the compound of formula 2-3' (6900 g, 13.41 mol, 1.0 eq) and 85% (mass fraction) N2H4·$H_2O$ (1580 g, 26.82 mol, 2.0 eq) were added to each flask under stirring. The mixtures were heated at reflux for 3 h, and the reactions were completed. The mixtures were cooled naturally and filtered under vacuum, and the filter cake was rinsed twice with THF (2 L×2). The filtrate was concentrated in a 50° C. water bath under reduced pressure to remove 24 L of THF, and the remaining filtrate was transferred to a 50 L reactor and heated at reflux. 95% ethanol (36 L) was slowly added, and a yellowish-green solid slowly precipitated. The mixture was stirred for 2 h. The mixture was cooled to room temperature and stirred for crystallization overnight. The mixture was filtered under vacuum, and the filter cake was rinsed once with 2 L of 95% ethanol and dried to give the compound of formula 2' as a yellowish-green powdered solid (4480 g, 100.0% HPLC purity, 86.9% yield).

$^1$HNMR (400 MHz, $CDCl_3$) δ(ppm): 7.38-7.36 (m, 9H), 7.25-7.22 (m, 6H), 5.43 (s, 2H), 2.46 (s, 3H).

Synthesis of Compound 2"

Step 1: Synthesis of 2-(5-methyl-4-nitro-1-(tetrahydro-2H-pyran-2-yl)-1H-pyrazol-3-yl)isoindoline-1,3-dione

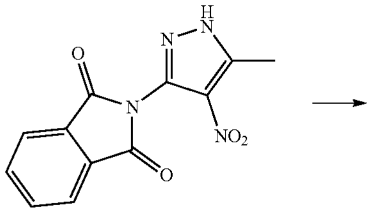

2-2

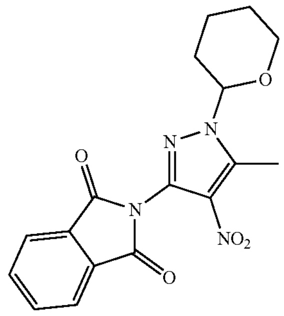

2-3"

To a reaction flask were added anhydrous acetonitrile (270 mol), p-toluenesulfonic acid (1.72 g, 0.01 mol, 0.1 eq) and pyridine (0.79 g, 0.01 mol, 0.1 eq), and the mixture was warmed to 50° C. and stirred for 2 h. The compound of formula 2-2 (27.2 g, 0.1 mol, 1.0 eq) was added. After the mixture was heated at reflux for 1 h, DHP (16.8 g, 0.2 mol, 2.0 eq) was added dropwise. After being refluxed for about 20 h, the reaction mixture was concentrated. The residue was slurried with ethyl acetate (90 mL) for 1 h and filtered, and the filter cake was dried to give the compound of formula 2-3" (28.6 g, 80.3% yield).

$^1$HNMR (400 MHz, DMSO-d6) δ (ppm): 8.08-7.98 (m, 4H), 5.76-5.71 (m, 1H), 4.01-3.75 (m, 2H), 2.76 (s, 3H), 2.30-2.16 (m, 1H), 1.98-1.94 (m, 2H), 1.72-1.67 (m, 1H), 1.57-1.56 (m, 2H).

Step 2: Synthesis of 5-methyl-4-nitro-1-(tetrahydro-2H-pyran-2-yl)-1H-pyrazol-3-amine

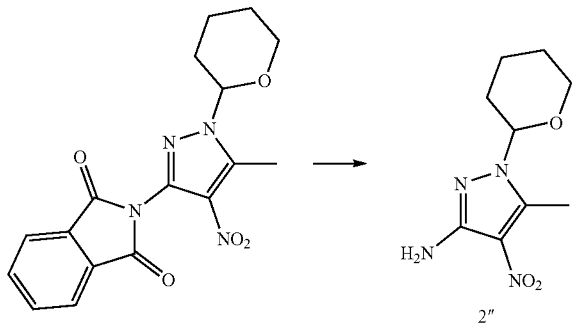

2-3″ 2″

To a reaction flask were added the compound of formula 2-3" (569.4 g, 1.6 mol, 1.0 eq) and THF (5.7 L). The mixture was heated at reflux, and hydrazine hydrate (85%) (141.1 g, 2.4 mol, 1.5 eq) was added dropwise over 0.5 h. The reaction mixture was refluxed for about another 8 h, and the reaction was completed as indicated by TLC (PE:EA=2:1). The reaction mixture was cooled to 20-25° C. and filtered under vacuum, and the filtrate was concentration to give a crude product (303 g). The crude product was added to 3 L of 95% ethanol, and the mixture was heated at reflux, cooled to room temperature, and filtered to give the compound of formula 2" as a yellowish-green solid. Yield=62.5%.

$^1$HNMR (400 MHz, DMSO-d6) δ (ppm): 6.15 (s, 2H), 5.42-5.38 (m, 1H), 3.91-3.87 (m, 1H), 3.69-3.65 (m, 1H), 2.58 (s, 3H), 2.17-1.98 (m, 1H), 1.98-1.93 (m, 1H), 1.81-1.76 (m, 1H), 1.66-1.52 (m, 3H).

Example 3

Synthesis of Compound of Formula 4', [(2-chlorophenyl)(4-((5-methyl-4-nitro-1-trityl-1H-pyrazol-3-yl)amino)-6-morpholinopyridin-3-yl)methanone]

Step 1: Synthesis of (6-chloro-4-((5-methyl-4-nitro-1-trityl-1H-pyrazol-3-yl)amino)pyridin-3-yl)(2-chlorophenyl)methanone

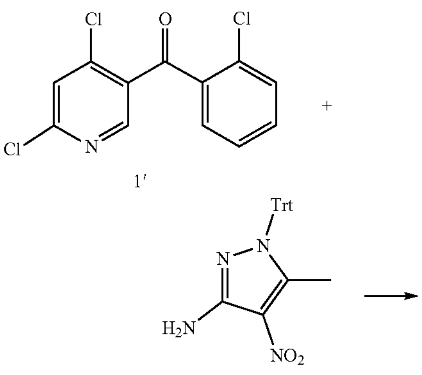

1′ 2′

-continued

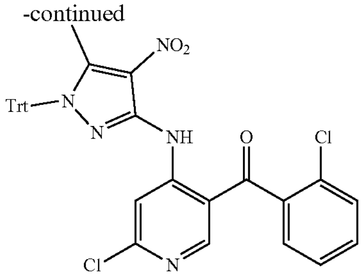

I′

NaH (10.0 g) was added to 2-MeTHF (600 mL). After the mixture was warmed to 50° C., the compound of formula 2' (38.4 g, 0.1 mol) was added. After the mixture was stirred for 1 h, the compound of formula 1' (28.5 g, 0.1 mol) was added. The mixture was allowed to react for 6-8 h, and the reaction was completed. The reaction mixture was cooled to 20-25° C., and acetic acid (9 g) was added dropwise, followed by the addition of 200 mL of water. The mixture was stirred, and the organic phase was separated and concentrated until about 100 mL was left, followed by the addition of ethanol (300 mL). After the mixture was refluxed for 4-6 h, the heating was stopped. The reaction mixture was cooled to 20-25° C. and then filtered, and the filter cake was dried to give the compound of formula I' as a yellow solid (41.4 g, 65.4% yield), which was directly used in the next step.

Step 2: Synthesis of (2-chlorophenyl)(4-((5-methyl-4-nitro-1-trityl-1H-pyrazol-3-yl)amino)-6-morpholinopyridin-3-yl)methanone

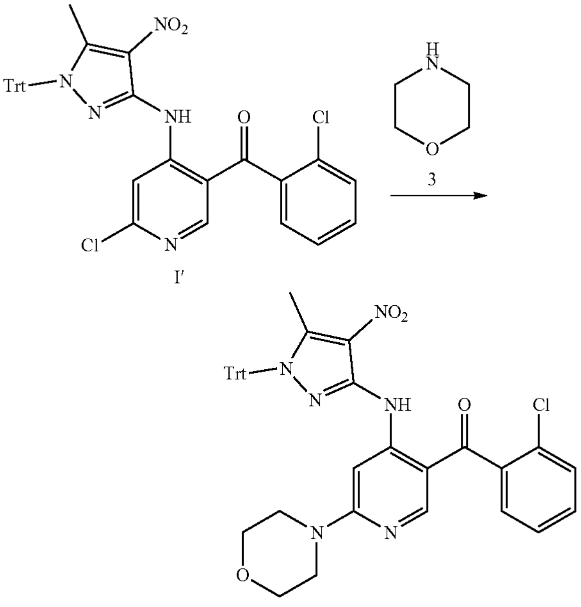

I′ 4′

The compound of formula I' (41.4 g), morpholine (17.1 g) and 2-MeTHF (400 mL) were added to a reaction flask and heated at 80° C. for 12-16 h. After the reaction mixture was concentrated until about 200 mL was left, ethanol (300 mL) was added at reflux. The reaction mixture was refluxed for 1 h, then cooled to 20-25° C., and filtered, and the filter cake was dried to give the compound of formula 4' as a yellow solid (41 g, 91.7% yield).

Example 4

Step 1: Synthesis of Compound of Formula 4", (2-chlorophenyl)(4-((5-methyl-4-nitro-1-(tetrahydro-2H-pyran-2-yl)-1H-pyrazol-3-yl)amino)-6-morpholinopyridin-3-yl methanone

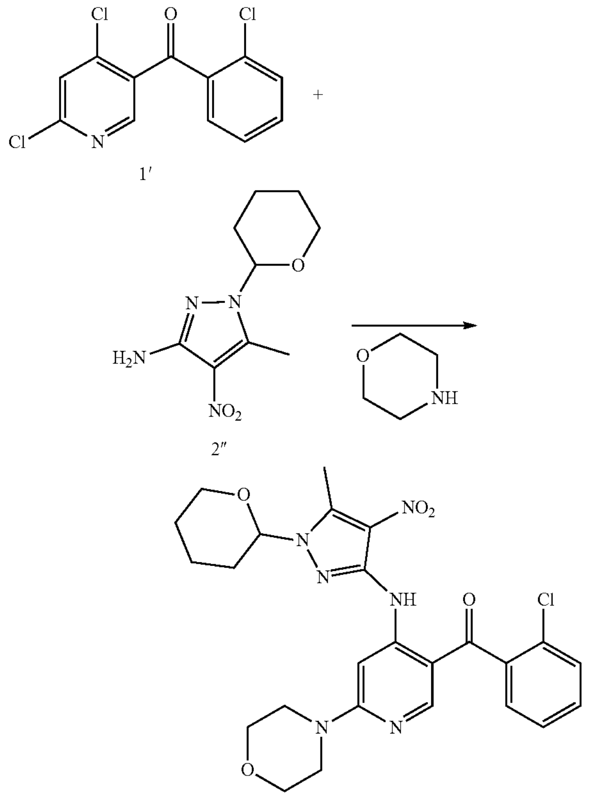

1'

2"

4"

60% (mass fraction) sodium hydrogen (87.36 g, 2.18 mol) was placed in a 10 L three-necked flask, and 2-MeTHF (4.3 L) was added. The system was milk white and turbid. The system was stirred at 45-50° C. for 1 h, and the compound of formula 2" (197.4 g, 0.87 mol) was added in batches. The system turned from yellow to brown. After 1 h of stirring, the compound of formula 1' (231.5 g, 0.81 mol) was added. The reaction mixture was allowed to reacted at 45-50° C. for 2.5 h, and the reaction was completed as indicated by HPLC in-process control. The temperature was lowered to 12° C., and acetic acid (78.61 g, 1.31 mol) was added in batches. The internal temperature was raised to 18° C., and then morpholine (228.3 g, 2.62 mol) was added. The reaction mixture was allowed to react at 90° C. for 15 h, and the reaction was completed as indicated by HPLC in-process control. The reaction mixture was cooled to 20-25° C., and 2 L of water was added. The organic phase was separated and concentrated, and the residue was slurried with 1 L of ethyl acetate for 2-4 h, followed by filtration, and the filter cake was dried in a forced air drying oven to give the compound of formula 4" as a yellow solid (218 g, 51.2% yield).

Step 2: Synthesis of Compound of Formula 7, 4-(5-(2-chlorophenyl)-3-methyl-2,10-dihydropyrazolo[4,3-b]pyrido[4,3-e][1,4]diazepin-8-yl)morpholine

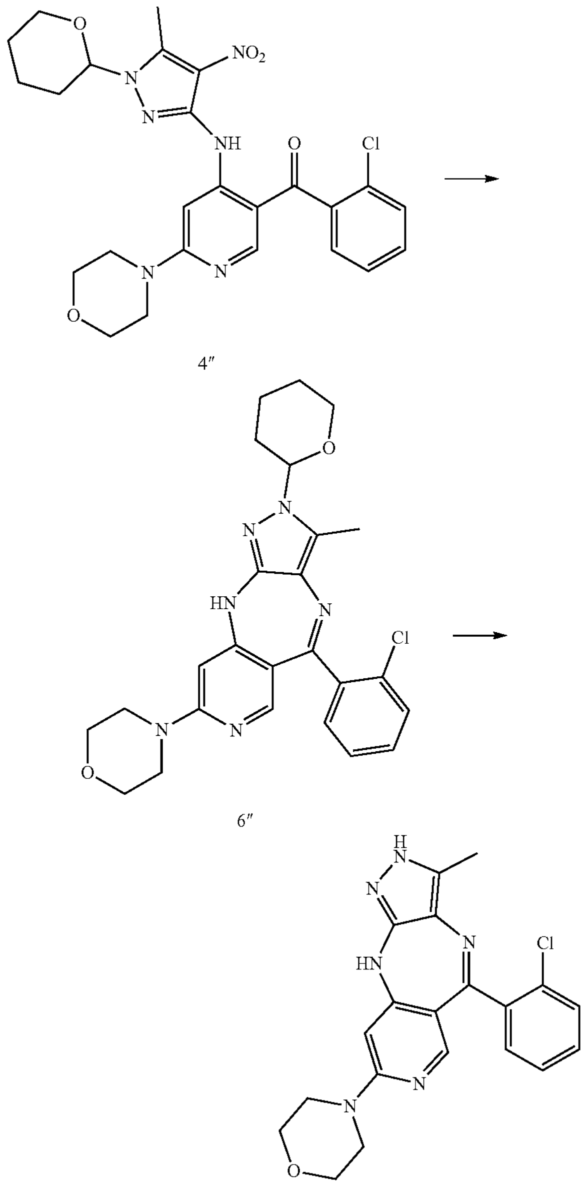

4"

6"

7

4" (1 g, 1.90 mmol) was dissolved in 60 mL of acetic acid, and 6 mL of water and 300 mg of Pd/C were added. The reaction mixture was allowed to react in a hydrogen atmosphere for 24 h and filtered, and the mother liquor was concentrated. 50 mL of water was added, and a yellow solid precipitate in large amounts. The solid was collected by filtration and dried to give the compound of formula 6" (720 mg, 80% yield).

6" (1 g, 2.09 mmol) was dissolved in methanol, and p-toluenesulfonic acid (0.43 g, 2.50 mmol) was added. The mixture was stirred at room temperature for 16 h, warmed to 55° C., supplemented with p-toluenesulfonic acid (0.28 g, 1.6 mmol), allowed to react for 3 h, and concentrated, and the residue was purified by column chromatography to give the product 7 as a yellow solid.

Molecular formula: $C_{20}H_{19}ClN_6O$; molecular weight: 394.86 LC-MS (Pos, m/z)=395.22 $[M+H]^+$.

Example 5

Synthesis of Compound of Formula 7

Step 1: Synthesis of Compound of Formula 4' (2-chlorophenyl)(4-((5-methyl-4-nitro-1-trityl-1H-pyrazol-3-yl)amino)-6-morpholinopyridin-3-yl) methanone

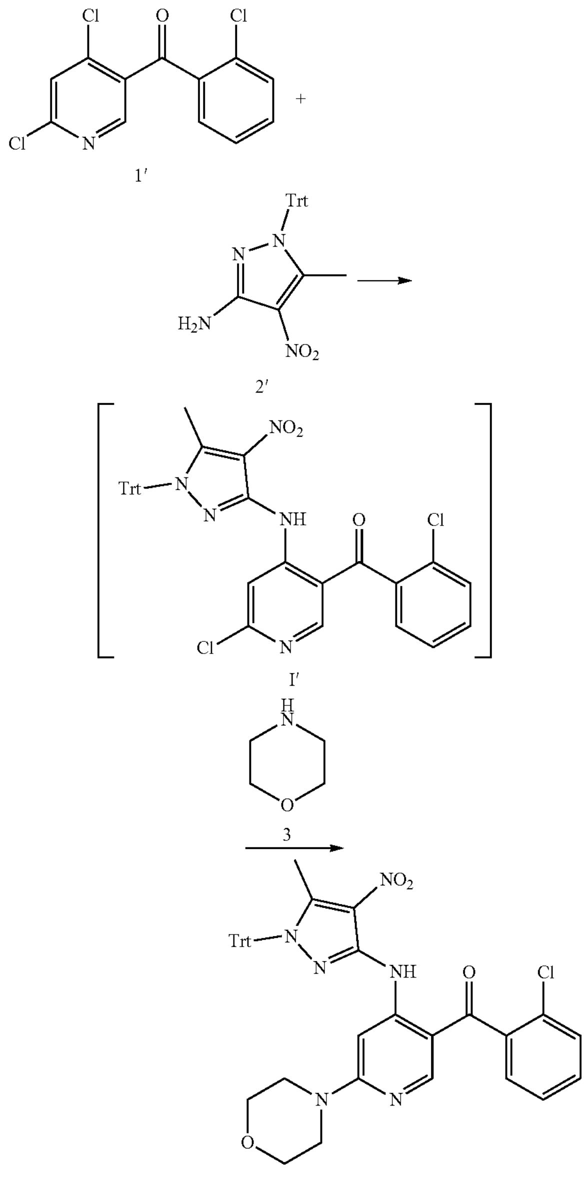

1' 2' I' 3 4'

To a reaction flask was added 2-MeTHF (15 L), followed by magnesium sulfate (500 g, 4.15 mol) and 60% (mass fraction) sodium hydride (260 g, 6.50 mol) under stirring, and the mixture was stirred at 50° C. for 2 h. The compound of formula 2' (1000 g, 2.60 mol) was added in batches, and the system turned brownish-yellow. After 1 h of stirring, the system turned brown. The compound of formula 1' (820 g, 2.86 mol) was added. The reaction mixture was allowed to react at 46-60° C. for 3.5 h, and the compound of formula 1' was completely reacted as indicated by HPLC in-process control. Acetic acid (234 g, 3.90 mol) was added in batches, and the system turned into a brown suspension. Morpholine (680 g, 7.80 mol) was added, and the system was refluxed for 15 h, and the reaction was completed as indicated by HPLC in-process control. The system was cooled to 15-25° C. 7.5 L of water was added, and the organic phase was separated, dried over anhydrous magnesium sulfate, and filtered. The filtrate was concentrated until about 1-2 L of solvent was left, and 5 L of toluene and 15 L of ethanol were added. Slurrying was performed at 78° C. for 2 h, and the mixture was cooled to room temperature and filtered. The filter cake was dried to give a yellow solid (1250 g, 70.3% yield).

$^1$HNMR (400 MHz, DMSO-d6) δ (ppm): 12.55 (s, 1H), 7.89 (s, 1H), 7.60-7.52 (m, 2H), 7.50-7.49 (m, 2H), 7.42-7.33 (m, 9H), 7.29-7.27 (m, 6H), 7.21 (s, 1H), 3.60-3.50 (m, 4H), 3.70 (s, 4H), 2.07 (s, 3H).

Step 2: Synthesis of Compound of Formula 5', (4-((4-amino-5-methyl-1-trityl-1H-pyrazol-3-yl) amino)-6-morpholinopyridin-3-yl)(2-chlorophenyl) methanone

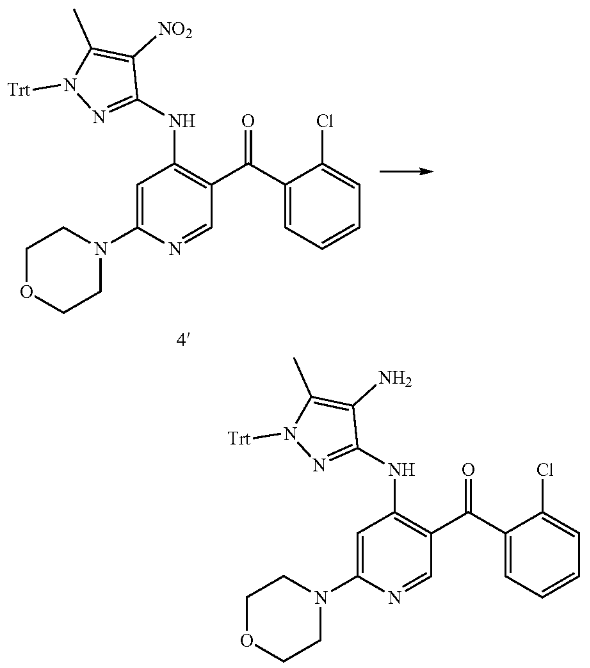

4' 5'

(Instance 1) To a 20 L reaction flask were added water (300 mL), ethanol (95%, 7.5 L), ammonium chloride (30.30 g, 0.57 mol) and iron powder (950 g, 17 mol), and the mixture was stirred at 55-60° C. for 1.5 h, followed by the addition of THF (7.5 L) and the compound of formula 4' (775 g, 1.13 mol). The reaction mixture was refluxed for 5 h, supplemented with iron powder (320 g, 5.66 mol), and refluxed for 15 h, and the reaction was completed as indicated by HPLC in-process control. The reaction mixture was filtered while hot through celite (1.5 kg), and the filter cake was rinsed with THF (3 L). The filtrate was concentrated until about 5 L of solvent was left, and 5 L of ethanol was added. Slurrying was performed at 65° C. for 3 h, and the mixture was cooled to room temperature and filtered. The filter cake was rinsed with 4 L of ethanol and dried to give a yellow solid (590 g, 79.6% yield).

$^1$HNMR (300 MHz, $CDCl_3$) δ(ppm): 11.42 (s, 1H), 8.04 (s, 1H), 7.47-7.23 (m, 19H), 7.11 (s, 1H), 3.67-3.63 (m, 4H), 3.27-3.24 (m, 4H), 1.59 (s, 3H).

(Instance 2) The compound of formula 4' (6.8 g, 10.0 mmol) and THF (150 mL) were added to an autoclave, followed by the addition of platinum oxide (700 mg), and hydrogen was introduced at 0.5-0.8 MPa. The reaction mixture was allowed to react at 40° C. for 46 h, and the reaction was completed as indicated by HPLC. The reaction mixture was filtered, and the filtrate was concentrated until about 50 mL was left, followed by the dropwise addition of 100 mL of n-heptane at reflux. The reaction mixture was cooled to room temperature and filtered, and the filter cake was dried to give a yellow solid (5.5 g, 84.6% yield).

Step 3: Synthesis of Compound of Formula 6', Iso-propanol-Complexed 4-(5-(2-chlorophenyl)-3-methyl-2-trityl-2,10-dihydropyrazolo[4,3-b]pyrido [4,3-e][1,4]diazepin-8-yl)morpholine trifluoroacetate

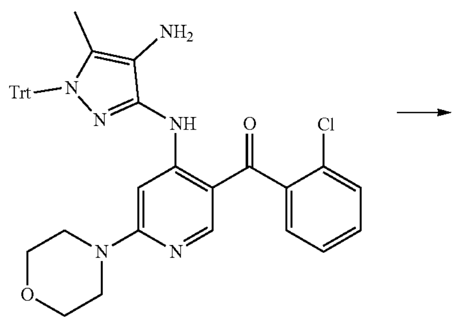

5'

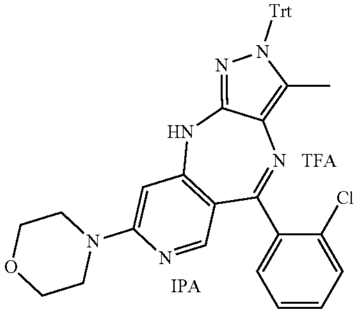

6'

20 L of isopropanol was added to a 50 L reactor, followed by the addition of the compound of formula 5' (1980 g, 3.03 mol) and TFA (690 g, 6.05 mol). After the reaction mixture was heated at reflux for 2 h, the reaction was completed as indicated by HPLC in-process control. The reaction mixture was cooled to 20° C. and filtered under vacuum, and the filter cake was rinsed with isopropanol until the filtrate was clear, and dried to give a yellow solid (2300 g, 93.8% yield).

$^1$HNMR (400 MHz, DMSO-d6) δ (ppm): 9.24 (s, 1H), 7.51-7.48 (m, 1H), 7.43-7.35 (m, 9H), 7.32-7.29 (m, 3H), 7.17-7.15 (m, 6H), 6.79 (s, 1H), 6.17 (s, 1H), 3.81-3.74 (m, 1H), 3.66-3.64 (m, 4H), 3.36-3.33 (m, 4H), 1.36 (s, 3H), 1.48-1.32 (d, 6H, J=6.12 Hz).

Step 4: Synthesis of Compound of Formula 7, 4-(5-(2-chlorophenyl)-3-methyl-2,10-dihydropyrazolo[4,3-b]pyrido[4,3-b][1,4]diazepin-8-yl)morpholine

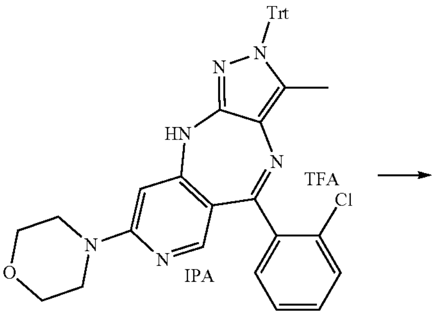

6'

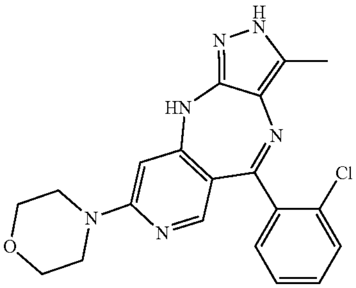

7

The compound of formula 6' (58.0 g, 71.5 mmol) and methanol (4.6 g, 143.7 mmol) were added to toluene (600 mL), followed by the addition of trifluoroacetic acid (8.2 g, 71.9 mmol). The reaction mixture was heated at reflux for 17 h, cooled to 50° C., and filtered, and the filter cake was slurried with toluene (400 mL) at 50° C. for 1 h. Then the mixture was filtered under vacuum, and the filter cake was dried in a forced air drying oven at 100° C. to give a yellow solid (32 g). The resulting solid was dissolved in methanol (300 mL) and water (100 mL). The pH of the solution was adjusted to 7-8 with aqueous ammonia (1-fold diluted), and a yellow solid precipitated in large amounts. The mixture was stirred at 50° C. for 1 h and filtered under vacuum, and the filter cake was dried to give a yellow solid (24 g, 99.7% purity, 85.4% yield).

$^1$H-NMR (DMSO-d6, 400 MHz) 11.57 (s, 1H), 8.29 (s, 1H), 7.32-7.47 (m, 4H), 6.89 (s, 1H), 5.95 (s, 1H), 3.61 (m, 4H), 3.31 (m, 4H), 1.97 (s, 3H).

Example 6

Step 1: Synthesis of Compound of Formula 7, 4-(5-(2-chlorophenyl)-3-methyl-2,10-dihydropyrazolo[4,3-b]pyrido[4,3-b][1,4]diazepin-8-yl)morpholine

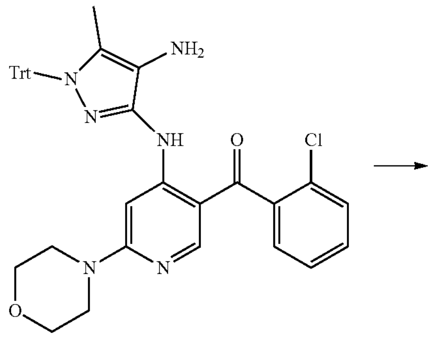

5'

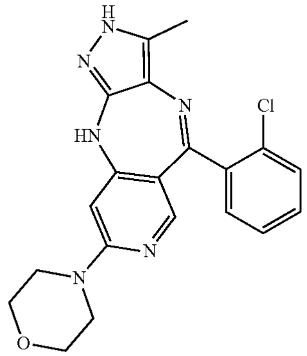

7

The compound of formula 5' (1 g, 1.53 mmol) was dissolved in DCM (10 mL), and TFA (350 mg, 3.06 mmol) was added. The system was stirred for 2.5 h, and a yellow solid precipitated. The system was heated at reflux and turned from a yellow turbid liquid into an orange clear liquid. The system was stirred overnight, and the reaction was performed for a total of 24 h. The system was black and clear. EA (100 mL) and a saturated aqueous sodium bicarbonate solution were added, and the organic phase was separated and concentrated. The residue was slurried with 20 mL of EA, and the mixture was filtered to give the compound of formula 7.

Example 7

The step of this example was similar to step 1 of Example 5. The compound of formula 4' was prepared by using toluene in place of 2-MeTHF.

Example 8

The step of this example was similar to step 1 of Example 5. The compound of formula 4' was prepared by using acetonitrile in place of 2-MeTHF.

Example 9

The step of this example was similar to step 1 of Example 5. The compound of formula 4' was prepared by using tetrahydrofuran in place of 2-MeTHF.

Example 10

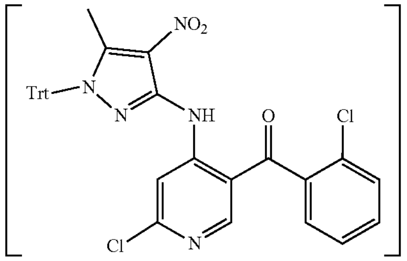

I'

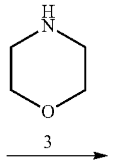

3

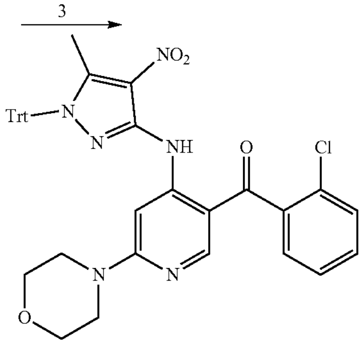

4'

The compound of formula I' (1.3 g, 2 mmol), morpholine (5 mL, 57 mmol) and potassium carbonate (2.0 g, 14.5 mmol) were added to DCM (10 mL). After the reaction mixture was heated at 40° C. for 2 h, the reaction was completed as indicated by HPLC, and the heating was stopped. The reaction mixture was filtered, and the filtrate was added to EtOH (10 mL). After the mixture was heated at reflux for 2 h, the heating was stopped. The reaction mixture was naturally cooled to 20-25° C. and filtered, and the filter cake was dried to give a product (1.2 g).

Example 11

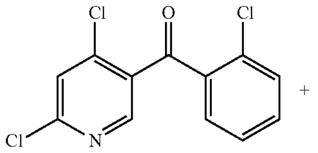

1'

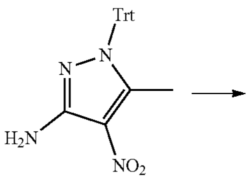

2'

-continued

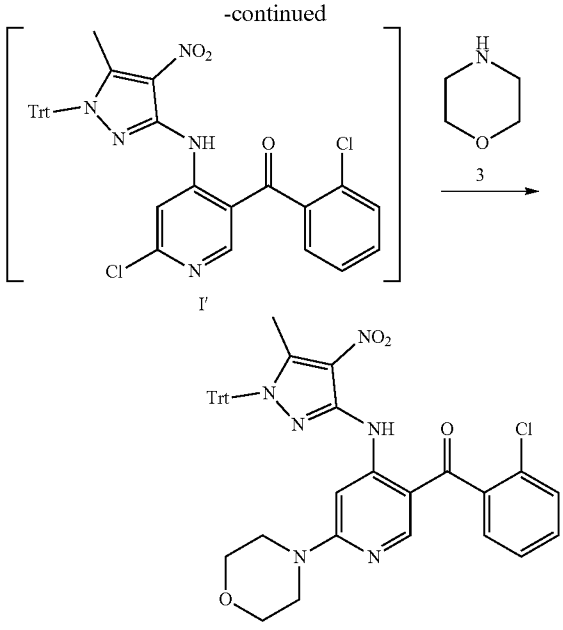

1'

4'

To a reaction flask was added 2-MeTHF (10 L), followed by 60% sodium hydrogen (300 g, 7.50 mol) under stirring. The mixture was warmed to 50° C., and the compound of formula 2' (1153.2 g, 3 mol) was added in batches. After 1 h of stirring, a solution of the compound of formula 1' (940.3 g, 3.3 mol) in 2-MeTHF (2 L) was added. The reaction mixture was allowed to react at 50° C. for 6 h, and the compound of formula 1' was completely reacted as indicated by TLC. The reaction mixture was cooled to 20° C., and acetic acid (270 g, 4.5 mol) was added dropwise and slowly. After 10 min of stirring, morpholine (784.8 g, 9 mol) was added. The reaction mixture was refluxed for 15 h, and the reaction was completed as indicated by HPLC in-process control. The heating was stopped, and the system was cooled to 15-25° C. The reaction mixture was washed with water (10 L×2), and the organic phase was dried over anhydrous $Na_2SO_4$ and filtered under vacuum. The filter cake was rinsed with 2-MeTHF (2 L). 200 g of activated carbon was added to the filtrate, and the filtrate was refluxed for 1 h and filtered while hot. The filter cake was rinsed with 2-MeTHF (1 L), and 6 L of solvent was evaporated from the filtrate at atmospheric pressure, followed by the addition of EtOH (8 L). The mixture was refluxed for 1 h, naturally cooled to 20-25° C. by stopping the heating, and filtered, and the filter cake was rinsed with EtOH (1 L). The wet product was transferred to DCM (15 L), and the resulting mixture was heated at reflux, followed by the addition of activated carbon (300 g). The mixture was stirred for 0.5 h and filtered while hot, and the filter cake was rinsed with DCM (1 L). 2 L of solvent was evaporated from the filtrate at atmospheric pressure, followed by the addition of EtOH (12 L). The mixture was stirred at reflux for 4 h, naturally cooled to 20-25° C. by stopping the heating, and filtered under vacuum, and the filter cake was dried to give a yellow solid (1234.5 g, 60.1% yield).

Example 12

The step of this example was similar to step 2 (instance 2) of Example 5. By using Pt/C in place of platinum oxide, the compound of formula 5' was prepared through reactions with a yield of 80% or more.

Example 13

The step of this example was similar to step 2 (instance 2) of Example 5. By using Pd/C in place of platinum oxide, the compound of formula 5' was prepared through reactions.

Example 14

The step of this example was similar to step 2 (instance 2) of Example 5. By using $Pd(OH)_2/C$ in place of platinum oxide, and the compound of formula 5' was prepared through reactions.

Example 15

The step of this example was similar to step 2 (instance 2) of Example 5. By using Rh/C in place of platinum oxide, the compound of formula 5' was prepared through reactions.

Example 16

The step of this example was similar to step 2 of Example 5. By using a mixture of THF and isopropanol in place of THF (instance 2), the compound of formula 5' was prepared through reactions.

Example 17

The step of this example was similar to step 3 of Example 5. By using p-toluenesulfonic acid in place of trifluoroacetic acid (TFA), the compound of formula 6' was prepared through reactions.

Example 18

The step of this example was similar to step 3 of Example 5. By using methanesulfonic acid in place of trifluoroacetic acid (TFA), the compound of formula 6' was prepared through reactions.

Example 19

The step of this example was similar to step 4 of Example 5. By using ethanol in place of methanol, the compound of formula 7 was prepared through reactions with a yield of 80% or more.

Example 20

The compound of formula 6' (385 g, 0.47 mol), TFA (138 g, 1.21 mol) and EtOH (55.66 g, 1.21 mol) were added to DCM (4 L). After the reaction mixture was heated at reflux for 1.5 h, the heating was stopped, and the reaction mixture was cooled to 20-25° C. A solution of NaOH (66 g) in water (2 L) was added, and a solid precipitated. The mixture was stirred for 1 h and filtered under vacuum. The filter cake was dissolved in 12 L of EtOH and 2 L of water, and 15 g of activated carbon was added. The mixture was stirred for 0.5 h and filtered under vacuum. The filtrate was concentrated until 1.5 L was left, then refluxed for 1 h, cooled to 20-25° C., and then filtered under vacuum, and the filter cake was dried to give a yellow solid (114 g, 61.0%).

The above description is only for the purpose of illustrating the preferred example of the present invention, and is not intended to limit the scope of the present invention. Any modifications, equivalents, improvements and the like made without departing from the spirit and principle of the present invention should be included in the protection scope of the present invention.

What is claimed is:

1. A method for synthesizing an anti-tumor compound of formula 7, comprising the following steps:

7

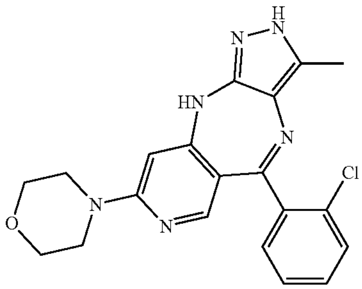

(a) subjecting a compound of formula 1 to an aromatic nucleophilic substitution reaction with a compound of formula 2M in an organic solvent under the action of a base to give a compound of formula IM, and subjecting the compound of formula IM, that is optionally separated, to another aromatic nucleophilic substitution reaction with a compound of formula 3, to give a compound of formula 4M;

(b) subjecting the compound of formula 4M to a reduction reaction in an organic solvent under the action of a catalyst to give a compound of formula 5M;

(c) subjecting the compound of formula 5M to a ring-closing reaction in an organic solvent under the action of an acid to give a compound of formula 6M; and (d) subjecting the compound of formula 6M to a reaction in an organic solvent to remove an amino-protecting group to give the anti-tumor compound of formula 7;

the reaction scheme is as follows:

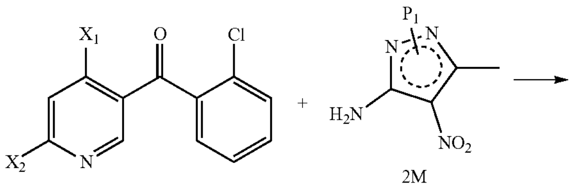

1

2M

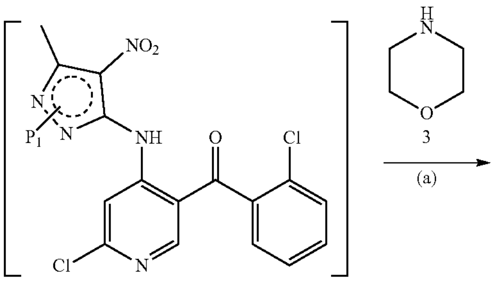

3

IM

-continued

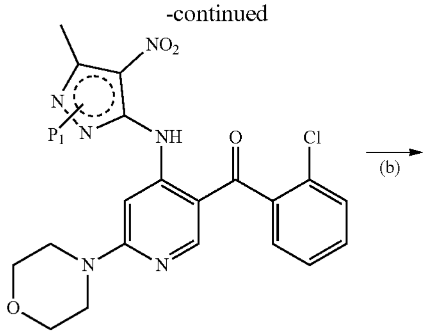

4M

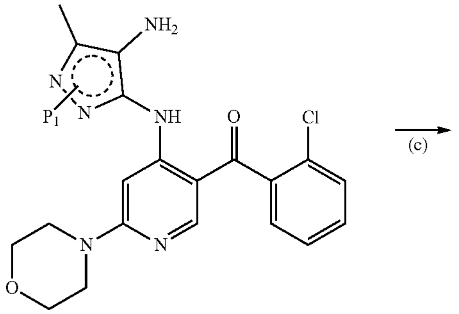

5M

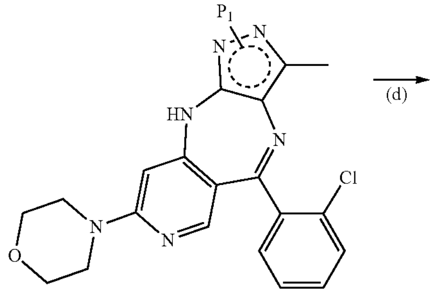

6M

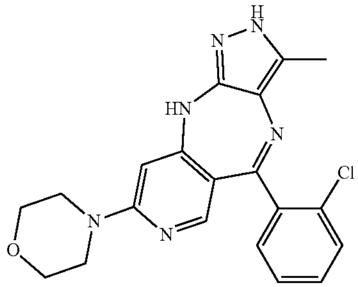

7 wherein $X_1$ and $X_2$ are each chlorine; $P_1$ is an amino-protecting group; $P_1$ is linked to any N atom in a ring where $P_1$ is located.

2. The method according to claim 1, wherein in step (a), the organic solvent is selected from one or more of 2-methyltetrahydrofuran, acetonitrile, tetrahydrofuran and toluene;

the base is selected from one or more of sodium hydride, sodium hydroxide, cesium carbonate, triethylene diamine, sodium tert-butoxide, potassium tert-butoxide, lithium bis(trimethylsilyl)amide and sodium hexamethyldisilazide;

in step (a), the reaction is performed at a pressure of 0 MPa to 10 MPa by gauge pressure;

the reaction is performed for a time period of 1-96 h; the reaction is performed at a temperature that is reflux temperature;

the aromatic nucleophilic substitution reaction of the compound of formula 1 with the compound of formula 2M under the action of the base is performed for a time period of 3-18 h at a temperature of 40° C. to 70° C.;

the another aromatic nucleophilic substitution reaction with the compound of formula 3 is performed for a time period of 8 h to 16 h, and is performed at a temperature that is reflux temperature;

the charging ratio is:

the solvent:the compound of formula 1: the compound of formula 2M:the compound of formula 3:the base=(0.5-60) L:(0.1-11) mol:1 mol:(0.3-30) mol:(0.2-25) mol.

3. The method according to claim 1, wherein in step (b), the organic solvent is selected from one or more of methanol, ethanol, isopropanol, tetrahydrofuran, 2-methyltetrahydrofuran, acetic acid and acetonitrile; the catalyst is selected from iron powder, platinum oxide, Pt/C, $Pd(OH)_2/C$, Rh/C and Pd/C;

in step (b), when the organic solvent comprises tetrahydrofuran, an amount of water is also added; the volume ratio of water to tetrahydrofuran is (0.2-2):10.

4. The method according to claim 1, wherein in step (c), the acid is selected from one or more of trifluoroacetic acid, methanesulfonic acid, p-toluenesulfonic acid, formic acid, acetic acid and hydrochloric acid; the organic solvent is selected from at least one of dichloromethane, methanol, ethanol and isopropanol;

in step (c), the reaction is performed for a time period of 1-96 h at a pressure of 0 MPa to 10 MPa by gauge pressure at a temperature that is reflux temperature; the charging ratio is: the solvent:the compound of formula 5M:the acid=(0.5-70) L:1 mol:0.220 mol.

5. The method according to claim 1, wherein step (c) is: allowing the compound of formula 5M to reflux in isopropanol under the action of trifluoroacetic acid for 1 h to 3 h.

6. The method according to claim 1, wherein in step (d), the organic solvent is selected from one or more of toluene, dichloromethane, acetonitrile, tetrahydrofuran, methanol, ethanol and isopropanol;

in step (d), an acid is also added, and the acid is selected from at least one of formic acid, acetic acid, hydrochloric acid, methanesulfonic acid and trifluoroacetic acid;

in step (d), in addition to the solvent, an alcohol or phenol is added; the alcohol is selected from methanol and/or ethanol, and the phenol is selected from phenol and/or p-methoxyphenol;

step (d), the reaction is performed for a time period of 1-96 h at a pressure of 0 MPa to 10 MPa by gauge pressure at a temperature that is reflux temperature; the charging ratio is: the solvent:the compound of formula 6M:the acid:the alcohol or phenol=(10-800) L:1 mol:(0.1-10) mol:(0.2-20) mol.

7. The method according to claim 1, further comprising steps of synthesizing the compound of formula 2M:

(i) subjecting a compound of formula 2-1 to a nitration reaction with nitric acid in a solvent selected from concentrated sulfuric acid, acetic anhydride or acetic acid for a time period of 0.5-2 h at a temperature of 10-20° C. to give a compound of formula 2-2;

(ii) subjecting the compound of formula 2-2 to an amino-protection reaction with an amino-protecting reagent in an organic solvent selected from one or more of tetrahydrofuran, 2-methyltetrahydrofuran, dichloromethane and acetonitrile for a time period of 1-48 h at a temperature of 60-100° C. to give a compound of formula (2-3) M; and (iii) subjecting the compound of formula (2-3) M to a reaction in an organic solvent selected from one or more of ethanol, tetrahydrofuran and acetonitrile, to remove a phthaloyl group to give a compound of formula 2M;

the reaction scheme being as follows:

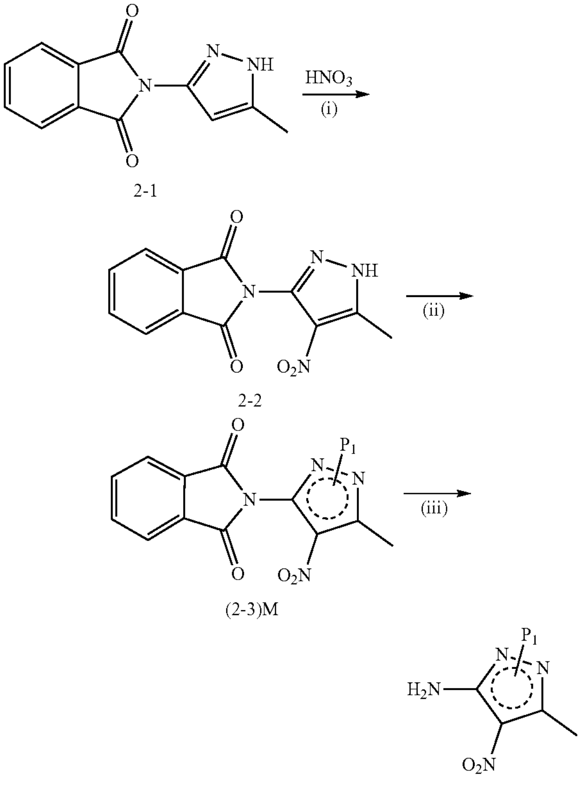

2-1

2-2

(2-3)M

2M wherein the amino-protecting reagent is $Boc_2O$, CbzCl, TosCl, FmocCl, PMBBr, MOMCl, EOMCl, tert-butanol, isobutylene, BnCl, acetic anhydride, SEMCl, TrtCl or DHP, is selected from Boc, Cbz, Tos, Fmoc, PMB, MOM, EOM, tBu, Bn, Ac, SEM, Trt and THP; $P_1$ is linked to any N atom in a ring where $P_1$ is located.

8. The method according to claim 7, wherein when the amino-protecting reagent is TrtCl, the reaction in step (ii) is performed under the following conditions: under the action of a base at 60° C. to 100° C. for 1 h to 48 h; alternatively, when the amino-protecting reagent is DHP, the reaction in step (ii) is performed under the following conditions: under the action of p-toluenesulfonic acid or pyridinium p-toluenesulfonate at 60° C. to 100° C. at reflux for 3 h to 48 h.

9. The method according to claim 1, further comprising a step of synthesizing the compound of formula 1:

subjecting a compound of formula 1-1 to a coupling reaction with a compound of formula 1-2 in an organic solvent for a time period of 2-4 h at a temperature of −70° C. to 60° C. to give the compound of formula 1;

the reaction scheme being as follows:

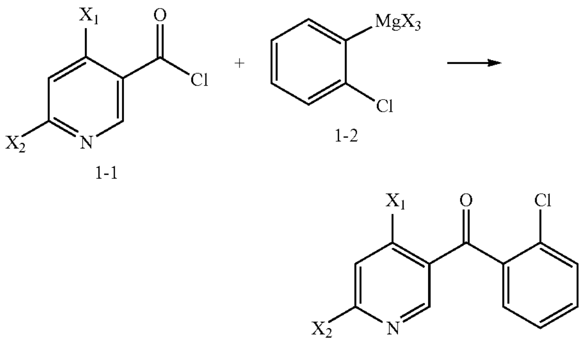

1-1

1-2

1 wherein $X_3$ is halogen; $X_1$, and $X_2$ are each chlorine.

10. An intermediate for preparing an anti-tumor compound of formula 7

7

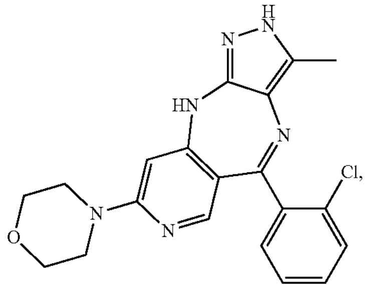

having the following structural formulas:

1

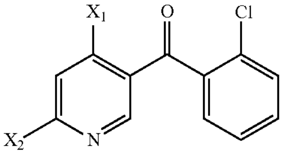

2M

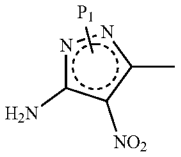

4M

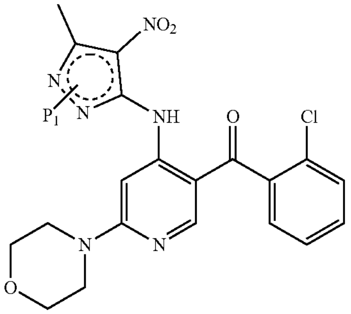

-continued

IM

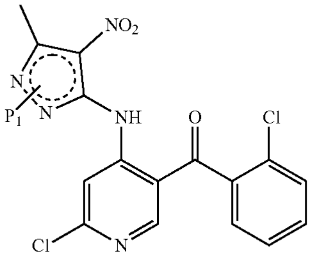

5M

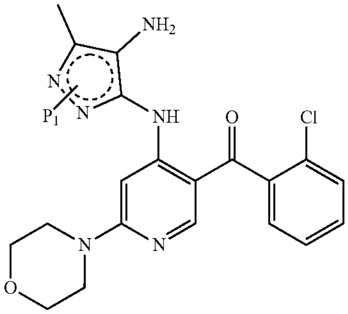

6M

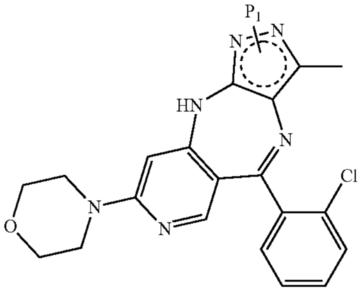

wherein, $X_1$ and $X_2$ are each independently chlorine;

$P_1$ is selected from Trt and THP; $P_1$ is linked to any N atom in a ring where $P_1$ is located.

11. An intermediate for preparing an anti-tumor compound of formula 7

7

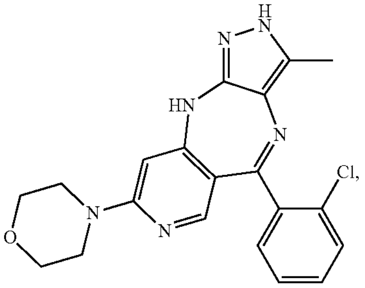

having the following structural formula;

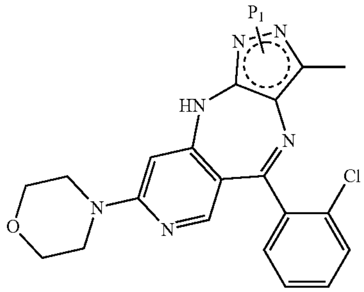

6M wherein $P_1$ is selected from Trt and THP; $P_1$ is linked to any N atom in a ring where $P_1$ is located;

the formula 6M is a complex comprising one molecule of trifluoroacetic acid and one molecule of isopropanol.

12. The method according to the claim 1, wherein in step (a), another aromatic nucleophilic substitution reaction with a compound of formula 3 is under alkaline conditions, to give a compound of formula 4M.

13. The method according to the claim 1, wherein $P_1$ is selected from Boc, Cbz, Tos, Fmoc, PMB, MOM, EOM, tBu, Bn, Ac, SEM, Trt and THP.

14. The method according to the claim 1, wherein $P_1$ is linked to the N atom ortho to the methyl group in the ring where $P_1$ is located.

15. The method according to the claim 2, wherein magnesium sulfate is added in the aromatic nucleophilic substitution reaction of the compound of formula 1 with the compound of formula 2M under the action of the base, and acetic acid is added in the another aromatic nucleophilic substitution reaction with the compound of formula 3, the charging ratio is:

the solvent:the compound of formula 1: the compound of formula 2M:the compound of formula 3:the base:magnesium sulfate:acetic acid=(0.5-60) L:(0.1-11) mol:1 mol:(0.3-30) mol:(0.2-25) mol:(0.2-20) mol:(0.1-15) mol.

16. The method according to the claim 12, wherein to provide the alkaline conditions in step (a), morpholine is used as a base instead of adding an additional base, or an additional base selected from one or more of sodium hydride, sodium hydroxide, cesium carbonate, triethylene diamine, sodium tert-butoxide, potassium tert-butoxide, lithium bis(trimethylsilyl)amide and sodium hexamethyldisilazide can be added.

17. The method according to the claim 3, wherein in step (b), when the catalyst is iron powder, the reaction is performed for a period of time of 1-96 h, at a pressure of 0 MPa to 10 MPa by gauge pressure, at a temperature that is reflux temperature, and ammonium chloride is also added in an amount of 0.05-5 molar equivalents; the solvent is a mixed solvent of ethanol and tetrahydrofuran, in an ethanol-to-tetrahydrofuran volume ratio of (6-10):10; the charging ratio is: the organic solvent: the compound of formula 4M:the catalyst=(1-130) L:1 mol:(1-150) mol, alternatively in step (b), when the catalyst is platinum oxide, Pt/C, $Pd(OH)_2$/C, Rh/C or Pd/C, the reaction is performed in a hydrogen atmosphere at 30° C. to 80° C. for 20 to 80 h; the reaction is performed at a pressure ranging from greater than 0 MPa to less than or equal to 10 MPa by gauge pressure; the charging ratio is: the solvent:the compound of formula 4M:the catalyst=(1-50) mL:1 g:(0.03-0.2).

18. The compound according to the claim 7, wherein $P_1$ is linked to the N atom ortho to the methyl group in the ring where $P_1$ is located.

19. The compound according to the claim 9, wherein $P_1$ is linked to the N atom ortho to the methyl group in the ring where $P_1$ is located.

20. The compound according to the claim 11, wherein $P_1$ is linked to the N atom ortho to the methyl group in the ring where $P_1$ is located.

* * * * *